(12) United States Patent
Cuevas-Cordobés et al.

(10) Patent No.: US 9,902,711 B2
(45) Date of Patent: *Feb. 27, 2018

(54) PIPERIDINE COMPOUNDS HAVING MULTIMODAL ACTIVITY AGAINST PAIN

(71) Applicant: LABORATORIOS DEL DR. ESTEVE S.A., Barcelona (ES)

(72) Inventors: Félix Cuevas-Cordobés, Valdemoro (ES); Carmen Almansa-Rosales, Barcelona (ES); Monica Garcia Lopez, Barcelona (ES); Eva Maria Ayet Galcera, Barcelona (ES); Maria Teresa Serafini Cabanes, Sabadell (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,398

(22) PCT Filed: Dec. 19, 2014

(86) PCT No.: PCT/EP2014/078811
§ 371 (c)(1),
(2) Date: Jun. 20, 2016

(87) PCT Pub. No.: WO2015/091988
PCT Pub. Date: Jun. 25, 2015

(65) Prior Publication Data
US 2017/0001979 A1    Jan. 5, 2017

(30) Foreign Application Priority Data

Dec. 20, 2013  (EP) .................................. 13384005

(51) Int. Cl.
*C07D 401/06* (2006.01)
*C07D 401/14* (2006.01)

(52) U.S. Cl.
CPC ......... *C07D 401/06* (2013.01); *C07D 401/14* (2013.01)

(58) Field of Classification Search
CPC .................................................. C07D 401/06
See application file for complete search history.

(56) References Cited

U.S. PATENT DOCUMENTS

| 5,495,022 A | 2/1996 | Baumgarth |
| 6,479,516 B1 | 11/2002 | Bronk |

FOREIGN PATENT DOCUMENTS

| EP | 0241053 | 10/1986 |
| EP | 0634398 | 1/1995 |
| EP | 1072592 A2 | 1/2001 |
| EP | 1072596 A2 | 1/2001 |
| GB | 2083476 A | 3/1982 |
| WO | 2011/137331 A2 | 11/2011 |

OTHER PUBLICATIONS

Johnson, A. W. Invitation to Organic Chemistry 1999 Jones and Bartlett: Mississauga, Canada, p. 24.*
Jones, Maitland Organic Chemistry Norton: New York, 1997, p. 84-99.*
Carson "N-Alkyl-4-[(8-azabicyclo[3.2.1]-oct-3-ylidene)phenylmethyl]-benzamides, mu and delta opioid agonists" Bioorganic & Medicinal Chemistry Letters 2004, 14, 2113-2116.*
Wei "N,N-Diethyl-4-(phenylpiperidin-4-ylidenemethyl)benzamide: A Novel, Exceptionally Selective, Potent δ Opioid Receptor Agonist with Oral Bioavailability and Its Analogues" J. Med. Chem. 2000, 43, 3895-3905.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
Stn-Chemical database registry # RN 1360321-02-3 entry for 4-(2-methoxyphenyl)-1-[(1-phenyl-1H-1,2,3-triazol-4-yl)methyl]-piperidine Entered STN: Mar. 7, 2012.*
Online "http://web.archive.org/web/20130122020518/http://www.chembridge.com/screening_libraries/" Jan. 22, 2013, accessed Nov. 30, 2016.*
RN 1329612-73-8 for 4-[[(3R,4R)-3-hydroxy-4-(3-methoxyphenyl)-1-piperidinyl]methyl]-1H-Pyrazole-3-carboxylic acid entered in STN Sep. 7, 2011.*
Online "http://web.archive.org/web/20100910093620/http://ambinter.com/orderinginfo.jsp" accessed Oct. 10, 2015, dated Sep. 9, 2010.*
Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Online "http://web.archive.org/web/20031225052253/http://www.specs.net/", accessed Apr. 1, 2015.*
Online "http://web.archive.org/web/20130122020518/http://www.chembridge.com/screening_libraries/" 2011, accessed Oct. 10, 2015.*
Database Pubchem, NCBI, Database Accession No. CID16667981, Aug. 17, 2007.
Database Pubchem, NCBI, Database Accession No. CID50963011, Mar. 29, 2011.
Database Pubchem, NCBI, Database Accession No. CID50977733, Mar. 29, 2011.

(Continued)

*Primary Examiner* — David K O'Dell
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to piperidene compounds having this pharmacological activity, to processes of preparation of such compounds, to pharmaceutical compositions comprising them, and to their use in therapy, in particular for the treatment of pain.

9 Claims, No Drawings

(56) References Cited

OTHER PUBLICATIONS

Database Pubchem, NCBI, Database Accession No. CID50984530, Mar. 29, 2011.
Ineke Van Wijangaarden, et al., Journal of Medicinal Chemistry, vol. 31, No. 10, p. 1934-1940, Oct. 1, 1988.
International Search Report for PCT/EP2014/078811 dated Feb. 4, 2015.

* cited by examiner

PIPERIDINE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid) and more particularly to piperidine compounds having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies.* Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. $\sigma_1$ receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding as a ligand to two different receptors relevant for the treatment of pain. This was mainly achieved by providing the compound according to the invention that bind both to the µ-opiod receptor and to the $\sigma_1$ receptor.

SUMMARY OF THE INVENTION

In this invention a family of structurally distinct piperidine derivatives which have a dual pharmacological activity towards both the sigma (σ) receptor, and the µ-opioid receptor was identified thus solving the above problem of identifying alternative or improved pain treatments by offering such dual compounds.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a very preferred embodiment if the compound has a binding expressed as $K_i$ which is <100 nm for both receptors, the µ-opioid receptor and the $\sigma_1$ receptor.

The invention is directed in a main aspect to a compound of general formula (I),

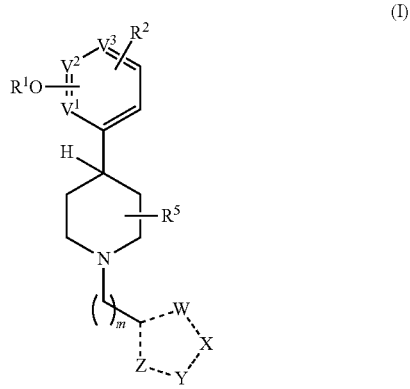

wherein $R^1$, $R^2$, $R^5$, $V^1$, $V^2$, $V^3$, W, X, Y, Z and m are as defined below in the detailed description.

DETAILED DESCRIPTION OF THE INVENTION

The invention is directed to a family of structurally distinct piperidine derivatives which have a dual pharmacological activity towards both the sigma (σ) receptor, and the µ-opiod receptor was identified thus solving the above problem of identifying alternative or improved pain treatments by offering such dual compounds.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a very preferred embodiment if the compound has a binding expressed as $K_i$ which is <100 nm for both receptors, the µ-opioid receptor and the $\sigma_1$ receptor.

The applicant has surprisingly found that the problem on which the present invention is based can be solved by using a multimodal balanced analgesic approach combining two different synergistic activities in a single drug (i.e., dual ligands which are bifunctional and bind to MOR and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of µ-opioid receptor agonists.

A dual compound that possess binding to both the µ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opiod therapies.

Advantageously, the dual compounds according to the present invention would in addition show one or more the following functionalities: $\sigma_1$ receptor antagonism and MOR agonism. It has to be noted, though, that both functionalities "antagonism" and "agonism" are also sub-divided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem,* 56, 1197-1210 (2013)].

In a particular aspect, the present invention is directed to compounds of general formula (I):

$$\text{(I)}$$

wherein
m is 1 or 2;
one of $V^1$, $V^2$ and $V^3$ is selected from nitrogen or carbon while the others are carbon;
$R^1$ is $COR^6$, $-CONR^8R^9$, $-COCR^6R^7NR^8R^9$, substituted or unsubstituted alkyl, substituted or unsubstituted cycloalkyl, substituted or unsubstituted aryl and substituted or unsubstituted heterocyclyl;
$R^2$ is hydrogen, halogen, $-NR^8R^9$, $-SR^7$, $-OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;
$R^5$ is hydrogen, halogen, hydroxy, substituted or unsubstituted O-alkyl, substituted or unsubstituted alkyl;
$R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or $R^6$ and $R^7$ or $R^8$ and $R^9$ together with their respective connecting carbon or nitrogen atom may form a cycloalkylic or heterocyclic 4 to 7-membered ring;
and wherein W, X, Y and Z are selected from carbon, nitrogen, or oxygen while W—X—Y—Z are forming together with the bridging C-atom, that is connected to the core scaffold, a 5-membered heterocyclic ring, which is either substituted on one of W, X, Y or Z by $$-\!\!\left(\!\!\begin{array}{c}R^4\\|\\C\\|\\H\end{array}\!\!\right)_{\!\!n}\!\!-R^3$$

or in which this said 5-membered heterocyclic ring—being otherwise unsubstituted—is fused at W and X to a further ringsystem;
wherein
n is 0 or 1;
$R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and
$R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment the compound according to the invention especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment the compound according to the invention especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment the compound according to the invention especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio.

In one embodiment one or more of the following provisos apply:
with the proviso that if $V^1$, $V^2$ and $V^3$ are carbon and either X or Y is $$C\!\!-\!\!\left(\!\!\begin{array}{c}R^4\\|\\C\\|\\H\end{array}\!\!\right)_{\!\!n}\!\!-R^3$$

with n=0 and $R^3$ being $CH_3$, then OR' may not be $OCH_3$ in meta position;
and/or
with the proviso that if $V^1$, $V^2$ and $V^3$ are carbon and either X or Y is $$C\!\!-\!\!\left(\!\!\begin{array}{c}R^4\\|\\C\\|\\H\end{array}\!\!\right)_{\!\!n}\!\!-R^3$$

then $R^3$ may not be alkyl;
and/or
with the proviso that if $V^1$, $V^2$ and $V^3$ are carbon and either X or Y is $$C\!\!-\!\!\left(\!\!\begin{array}{c}R^4\\|\\C\\|\\H\end{array}\!\!\right)_{\!\!n}\!\!-R^3$$

then $R^5$ may not be OH; and/or with the proviso that the compound may not be 3-Piperidinol, 4-(3-methoxyphenyl)-1-[(2-methyl-1H-imidazol-5-yl)methyl];

and/or with the proviso that the compound may not be 1H-Pyrazole-3-carboxylic acid, 4-[[(3R,4R)-3-hydroxy-4-(3-methoxyphenyl)-1-piperidinyl]methyl].

When different radicals $R^1$ to $R^8$ are present simultaneously in the different Formulas of the present invention they may be identical or different.

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, 010-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{1-6}$-alkenyl like ethylene, propylene, butylene, pentylene, or hexylene; or is $C_{1-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by F, Cl, Br, I, $NH_2$, SH or OH, —C(O)OH, or —$OC_{1-4}$alkyl being unsubstituted or substituted by one or more of OH or halogen (F, Cl, I, Br). More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$.

Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted by one or more of halogen (F, Cl, I, Br), —OH, —$NH_2$, —SH, —C(O)OH, or —$OC_{1-4}$alkyl being unsubstituted or substituted by one or more of OH or halogen (F, Cl, I, Br).

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through a $C_{1-6}$-alkyl (see above) which may be branched or linear and is unsubstituted or substituted once or several times. Thus, in the context of this invention alkylaryl is understood as meaning an aryl group (see above) being connected to another atom through a $C_{1-6}$-alkyl (see above). The alkyl may be branched or linear and is unsubstituted, while the aryl may be unsubstituted or substituted once or several times. Preferably, alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning a heterocyclyl group being connected to another atom through a $C_{1-6}$-alkyl (see above) which may be branched or linear and is unsubstituted or substituted once or several times. In the context of this invention alkylheterocyclyl is understood as meaning a heterocyclyl group being connected to another atom through a $C_{1-6}$-alkyl (see above). The alkyl may be branched or linear and is unsubstituted, while the heterocylyl may be unsubstituted or substituted once or several times. Preferably alkylheterocyclyl is understood as meaning a heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning a cycloalkyl group being connected to another atom through a $C_{1-6}$-alkyl (see above) which may be branched or linear and is unsubstituted or substituted once or several times. Thus, in the context of this invention alkylcycloalkyl is understood as meaning a cycloalkyl group being connected to another atom through a $C_{1-6}$-alkyl (see above). The alkyl may be branched or linear and is unsubstituted, while the cycloalkyl may be unsubstituted or substituted once or several times. Preferably alkylcycloalkyl is understood as meaning a cycloalkyl group (see above) being connected to another atom through 1 to 4 (—$CH_2$—) groups. Most preferably alkylcycloalkyl is —$CH_2$— cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, indene, 2,3-dihydroindene (indane), tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, indene, 2,3-dihydroindene, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aryl (including alkyl-aryl), cycloalkyl (including alkyl-cycloalkyl) or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

Most preferably in connection with aryl (including alkyl-aryl), substituted is understood in the context of this invention that any aryl (including alkyl-aryl), which is substituted is substituted by one or more of halogen (F, Cl, I, Br), —OH, —NH$_2$, —SH, —C(O)OH, —OC$_{1-4}$alkyl being unsubstituted or substituted by one or more of OH or halogen (F, Cl, I, Br), —CN, or —C$_{1-4}$alkyl being unsubstituted or substituted by one or more of OH or halogen (F, Cl, I, Br).

Most preferably in connection with cycloalkyl (including alkyl-cycloalkyl) or heterocyclyl (including alkyl-heterocyclyl), substituted is understood in the context of this invention that any cycloalkyl and heterocyclyl (also in an alkyl-cycloalkyl or alkylheterocyclyl) which is substituted is substituted by one or more of halogen (F, Cl, I, Br), —OH, —NH$_2$, —SH, =O, —C(O)OH, —OC$_{1-4}$alkyl being unsubstituted or substituted by one or more of OH or halogen (F, Cl, I, Br), —CN, or —C$_{1-4}$alkyl being unsubstituted or substituted by one or more of OH or halogen (F, Cl, I, Br).

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with ∇ or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—).

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts. This applies also to its solvates or prodrugs.

In a preferred embodiment of the compound according to the invention according to general formula I

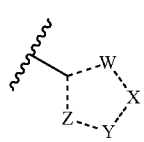

—while being either substituted on one of W, X, Y or Z by

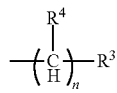

or being fused at W and X to a further ringsystem to the 5-membered heterocyclic ring formed by W—X—Y—Z while being otherwise unsubstituted—is selected from:

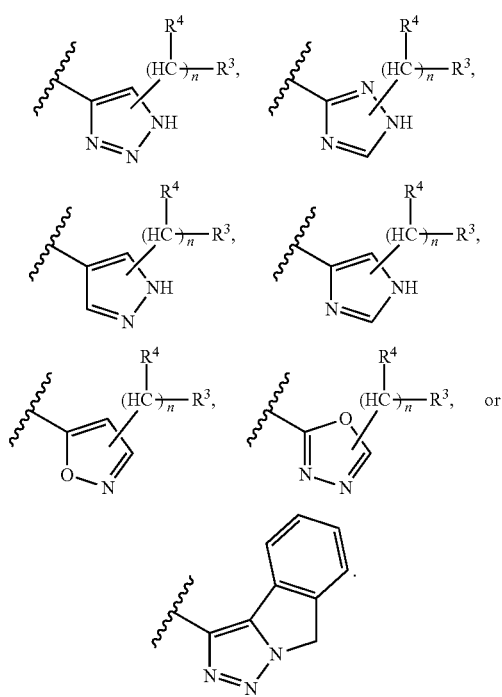

In another preferred embodiment of the compound according to the invention according to general formula I

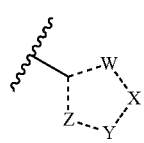

—while being either substituted on one of W, X, Y or Z by

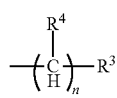

or being fused at W and X to a further ringsystem to the 5-membered heterocyclic ring formed by W—X—Y—Z while being otherwise unsubstituted—is selected from

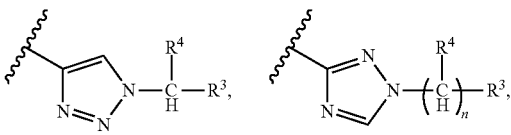

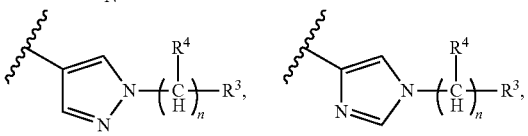

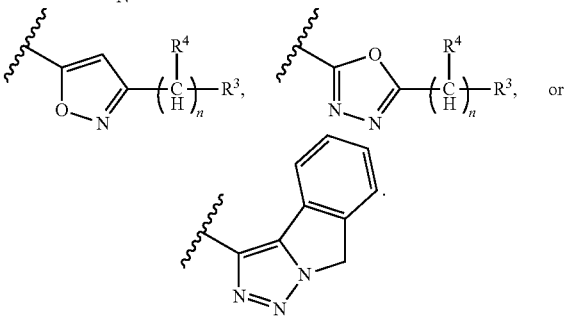

In another preferred embodiment of the compound according to the invention according to general formula I

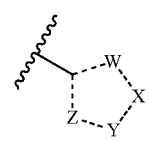

—while being either substituted on one of W, X, Y or Z by

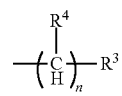

or being fused at W and X to a further ringsystem to the 5-membered heterocyclic ring formed by W—X—Y—Z while being otherwise unsubstituted—is selected from

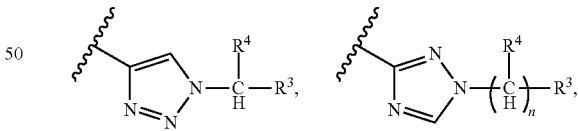

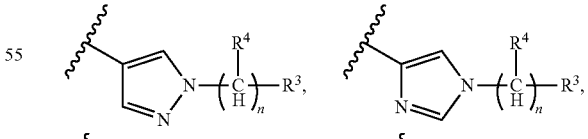

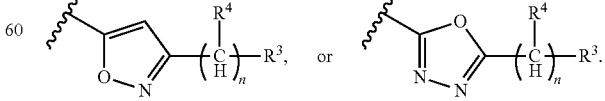

In a further preferred embodiment of the compound according to the invention according to general formula I the compound is a compound according to Formula II, (II)

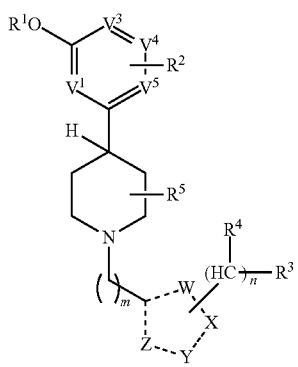

wherein m is 1 or 2;

n is 0 or 1;

one of $V^1$, $V^3$, $V^4$ and $V^5$ is selected from nitrogen or carbon while the others are carbon;

$R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl;

$R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and $R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^5$ is hydrogen, halogen, hydroxy, substituted or unsubstituted O-alkyl, substituted or unsubstituted alkyl;

$R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or $R^6$ and $R^7$ or $R^8$ and $R^9$ together with their respective connecting carbon or nitrogen atom may form a cycloalkylic or heterocyclic 4 to 7-membered ring;

and wherein W, X, Y and Z are selected from carbon, nitrogen, or oxygen while W—X—Y—Z are forming together with the bridging C-atom, that is connected to the core scaffold, a 5-membered heterocyclic ring, or wherein

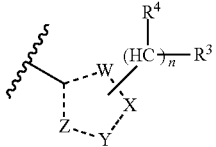 is 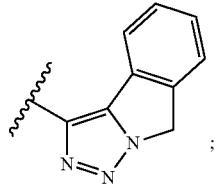;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof or a corresponding solvate thereof.

In one related and also preferred embodiment of the compound according to the invention according to general formula I wherein the compound is a compound according to Formula II as described, W, X, Y and Z are—while all other radicals remain identically defined—selected from carbon, nitrogen, or oxygen while W—X—Y—Z are forming together with the bridging C-atom, that is connected to the core scaffold, a 5-membered heterocyclic ring.

In one embodiment one or more of the following provisos apply:

with the proviso that if $V^1$, $V^3$, $V^4$ and $V^5$ are carbon and either X or Y is

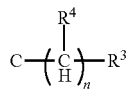

with n=0 and $R^3$ being $CH_3$, then $R^1$ may not be $CH_3$;

with the proviso that if $V^1$, $V^3$, $V^4$ and $V^5$ are carbon and either X or Y is

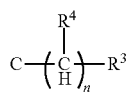

then $R^3$ may not be alkyl; and/or with the proviso that if $V^1$, $V^3$, $V^4$ and $V^5$ are carbon and either X or Y is

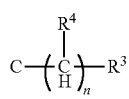

then $R^5$ may not be OH.

In a preferred embodiment of the compound according to the invention according to general formula II

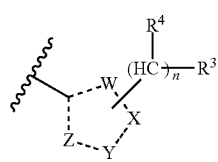

is selected from:

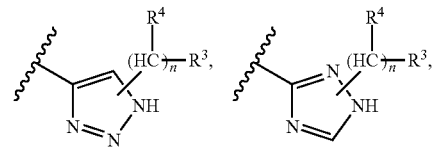

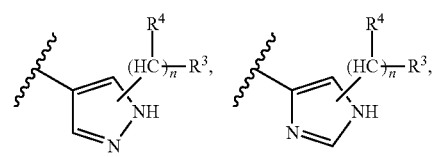

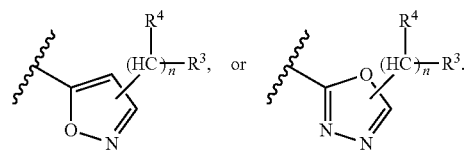

In another preferred embodiment of the compound according to the invention according to general formula II

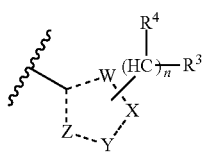

is selected from

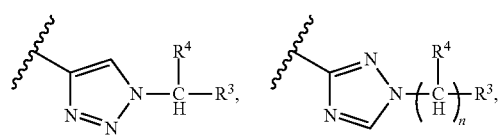

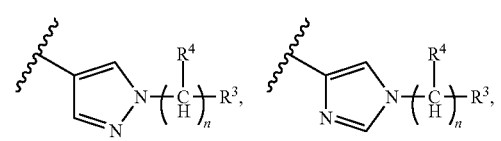

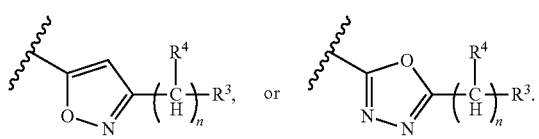

In another preferred embodiment of the compound according to the invention according to general formulas I or II the compound is a compound according to Formula III,

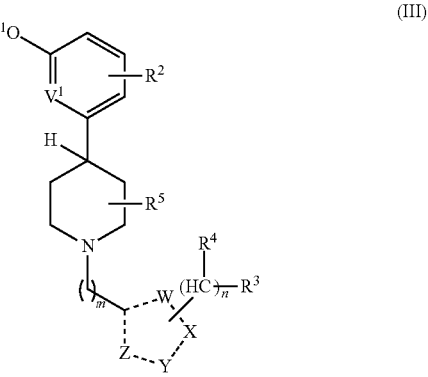

wherein m is 1 or 2;

n is 0 or 1;

$V^1$ is selected from nitrogen or carbon;

$R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl;

$R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and $R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^5$ is hydrogen, halogen, hydroxy, substituted or unsubstituted O-alkyl, substituted or unsubstituted alkyl;

$R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or $R^6$ and $R^7$ or $R^8$ and $R^9$ together with their respective connecting carbon or nitrogen atom may form a cycloalkylic or heterocyclic 4 to 7-membered ring;

and

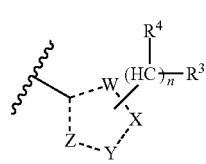

is selected from:

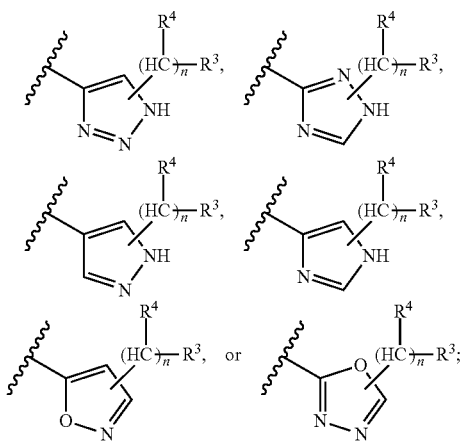

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof or a corresponding solvate thereof.

In one embodiment one or more of the following provisos apply:
with the proviso that if $V^1$ is carbon and

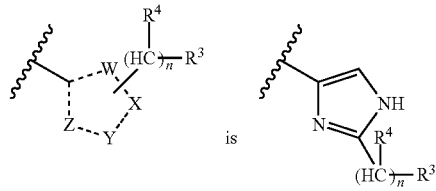

then $R^3$ may not be alkyl;
with the proviso that if $V^1$ is carbon and

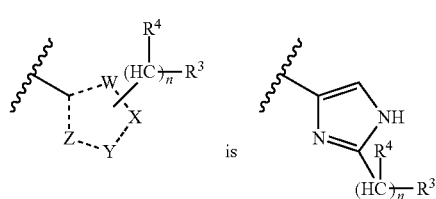

then $R^5$ may not be OH; and/or
with the proviso that if $V^1$ is carbon and

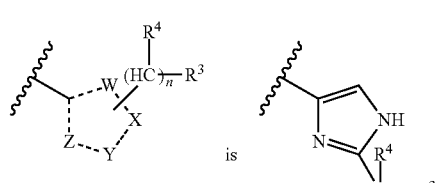

with n=0 and $R^3$ being $CH_3$, then $R^1$ may not be $CH_3$; and/or with the proviso that the compound is not 3-Piperidinol, 4-(3-methoxyphenyl)-1-[(2-methyl-1H-imidazol-5-yl) methyl].

In a preferred embodiment of the compound according to the invention according to general formula III

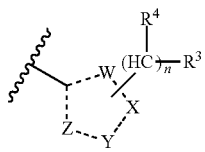

is selected from:

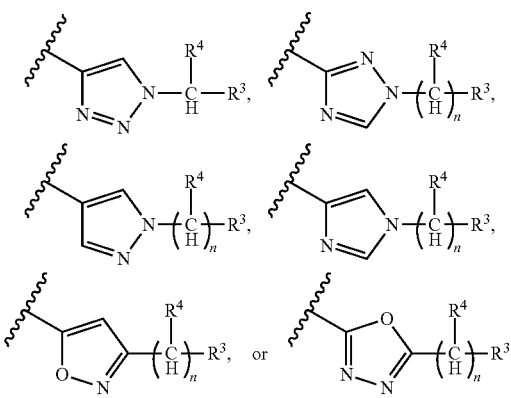

In another preferred embodiment of the compound according to the invention according to general formulas I or II the compound is a compound according to Formula Ib (Ib)

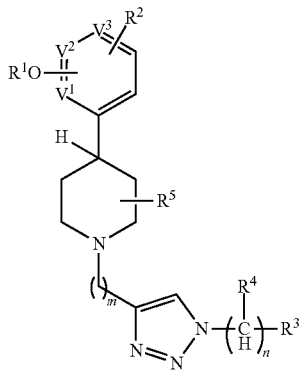

wherein
m is 1 or 2;
n is 0 or 1;
one of $V^1$, $V^2$ and $V^3$ is selected from nitrogen or carbon while the others are carbon;
$R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl;
$R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

R³ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and R⁴ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

R⁵ is hydrogen, halogen, hydroxy, substituted or unsubstituted O-alkyl, substituted or unsubstituted alkyl; and R⁶, R⁷, R⁸ and R⁹ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or R⁶ and R⁷ or R⁸ and R⁹ together with their respective connecting carbon or nitrogen atom may form a cycloalkylic or heterocyclic 4 to 7-membered ring;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof or a corresponding solvate thereof.

In another preferred embodiment of the compound according to the invention according to general formulas I or II the compound is a compound according to Formula IV,

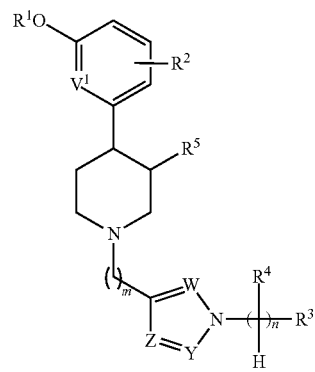

(IV)

wherein m is 1 or 2;

n is 0 or 1;

V¹ is selected from nitrogen or carbon;

R¹ is —COR⁶, —CONR⁸R⁹, —COCR⁶R⁷NR⁸R⁹, substituted or unsubstituted alkyl, substituted or unsubstituted cycloalkyl, substituted or unsubstituted aryl and substituted or unsubstituted heterocyclyl;

R² is hydrogen, halogen, —NR⁸R⁹, —SR⁷, —OR⁷, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

R³ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and R⁴ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

R⁵ is hydrogen, halogen, hydroxy, substituted or unsubstituted O-alkyl, substituted or unsubstituted alkyl;

R⁶, R⁷, R⁸ and R⁹ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or R⁶ and R⁷ or R⁸ and R⁹ together with their respective connecting carbon or nitrogen atom may form a cycloalkylic or heterocyclic 4 to 7-membered ring;

and W, Y and Z are independently from one another selected from N or CH with only 1 or 2 of them being CH;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention according to general formula IV above

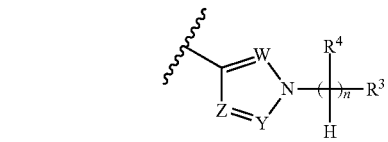

is selected from:

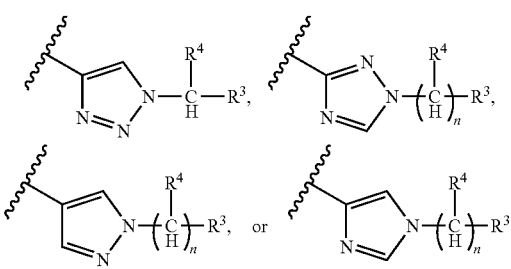

In another preferred embodiment of the compound according to the invention according to general formulas I, II, and III the compound is a compound according to Formula IV,

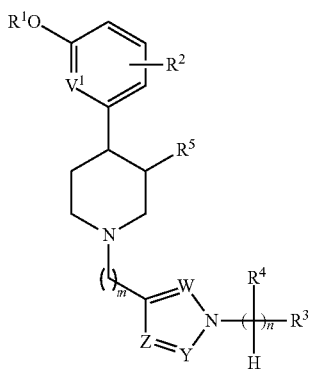

(IV)

wherein m is 1 or 2;

n is 0 or 1;

$V^1$ is selected from nitrogen or carbon;

$R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl;

$R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and $R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;

$R^5$ is hydrogen, halogen, hydroxy, substituted or unsubstituted O-alkyl, substituted or unsubstituted alkyl;

$R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl; or $R^6$ and $R^7$ or $R^8$ and $R^9$ together with their respective connecting carbon or nitrogen atom may form a cycloalkylic or heterocyclic 4 to 7-membered ring;

and

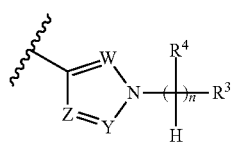

is selected from:

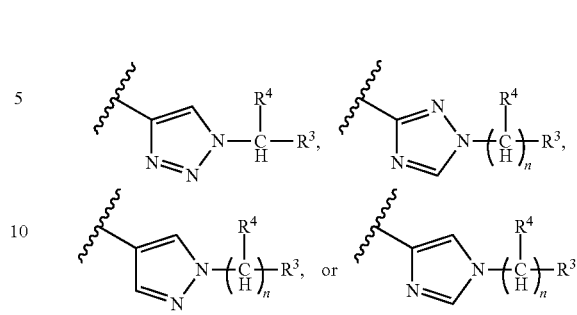

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention according to general formulas I, II, III or IV $R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or the alkyl is selected from $C_{1-8}$alkyl like methyl, ethyl, propyl, butyl, pentyl, hexyl, heptyl, octyl; preferably is $C_{1-6}$alkyl like methyl, ethyl, propyl, butyl, pentyl, hexyl; more preferably is $C_{1-4}$alkyl, like methyl, ethyl, propyl and butyl;

and/or the cycloalkyl is selected from $C_{3-8}$cycloalkyl; preferably is $C_{3-7}$cycloalkyl; more preferably is selected from cyclopropyl, cyclobutyl, cyclopentyl or cyclohexyl;

and/or most preferably $R^1$ is —$COR^6$, —$CONR^8R^9$, —$COCR^6R^7NR^8R^9$, substituted or unsubstituted alkyl like $C_{1-4}$-alkyl or $CH_3$, $C_2H_4OCH_3$, $C_3H_6OCH_3$, and/or $R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;

and/or halogen is any of fluorine, chlorine, iodine or bromine, preferably chlorine or fluorine;

and/or most preferably $R^2$ is selected from hydrogen, halogen like fluorine, or $C_{1-4}$alkyl like $CH_3$ or $CF_3$;

and/or $R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl or $R^3$ is not alkyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or preferably $R^3$ is not alkyl;

and/or most preferably $R^3$ is selected from substituted or unsubstituted alkyl like propyl or butyl, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine, or most preferably $R^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;

and/or $R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or most preferably $R^4$ is selected from hydrogen or from substituted or unsubstituted $C_{1-4}$alkyl like $CH_3$ or $CH_2OH$;

and/or $R^5$ is hydrogen, halogen, hydroxy, substituted or unsubstituted O-alkyl, substituted or unsubstituted alkyl, wherein
the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the O-alkyl is —O—$C_{1-8}$alkyl like —Omethyl, —O-ethyl, —O-propyl, —O-butyl, —O-pentyl, —O-hexyl, —O-heptyl, or —O-octyl; preferably is —O—$C_{1-6}$alkyl like —O-methyl, —O-ethyl, —O-propyl, —O-butyl, —O-pentyl, or —O-hexyl; more preferably is —O—$C_{1-4}$alkyl like —O-methyl, —O-ethyl, —O-propyl or —O-butyl;

and/or halogen is any of fluorine, chlorine, iodine or bromine, preferably chlorine or fluorine;

and/or most preferably $R^5$ is selected from hydrogen or hydroxy;

and/or $R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl, or $R^6$ and $R^7$ or $R^8$ and $R^9$ together with their respective connecting carbon or nitrogen atom may form a cycloalkylic or heterocyclic 4 to 7-membered ring, wherein
the aryl is phenyl, naphtyl or anthracene; preferably is napthyl and phenyl; more preferably is phenyl;

and/or the alkyl-aryl is $C_{1-4}$-alkyl-aryl; preferably is benzyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or when $R^6$ and $R^7$ or $R^8$ and $R^9$ together with their respective connecting carbon or nitrogen atom form a cycloalkylic or heterocyclic ring this ring is 5 or 6 membered, preferably $R^6$ and $R^7$ together with their respective connecting carbon atom form a saturated cycloalkylic ring of 5 or 6 members, more preferably $R^6$ and $R^7$ together with their respective connecting carbon atom form saturated, unsubstituted cyclohexyl; and/or most preferably $R^6$, $R^7$, $R^8$ and $R^9$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkylaryl like benzyl, or $R^6$ and $R^7$ together with their connecting carbon atom form a cycloalkylic 5 or 6-membered ring like cyclohexyl.

In a preferred embodiment of the compound according to the invention according to general formulas I, II, III or IV $R^1$ is —$COR^6$, —$CONR^8R^9$, —$COCR^6R^7NR^8R^9$, substituted or unsubstituted alkyl, substituted or unsubstituted cycloalkyl, substituted or unsubstituted aryl and substituted or unsubstituted heterocyclyl, wherein the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;
and/or
the alkyl is selected from $C_{1-8}$alkyl like methyl, ethyl, propyl, butyl, pentyl, hexyl, heptyl, octyl; preferably is $C_{1-6}$alkyl like methyl, ethyl, propyl, butyl, pentyl, hexyl; more preferably is $C_{1-4}$alkyl, like methyl, ethyl, propyl and butyl;
and/or
the cycloalkyl is selected from $C_{3-8}$cycloalkyl; preferably is $C_{3-7}$cycloalkyl; more preferably is selected from cyclopropyl, cyclobutyl, cyclopentyl or cyclohexyl.

In another preferred embodiment of the compound according to the invention according to general formulas I, II, III or IV $R^1$ is —$COR^6$, —$CONR^8R^9$, —$COCR^6R^7NR^8R^9$, substituted or unsubstituted alkyl like $C_{1-4}$-alkyl or $CH_3$, $C_2H_4OCH_3$, $C_3H_6OCH_3$, In another preferred embodiment of the compound according to the invention according to general formulas I, II, III or IV $R^2$ is hydrogen, halogen, —$NR^8R^9$, —$SR^7$, —$OR^7$, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;
and/or
the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;
and/or
the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;
and/or
the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;
and/or
the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;
and/or
halogen is any of fluorine, chlorine, iodine or bromine, preferably chlorine or fluorine.

In another preferred embodiment of the compound according to the invention according to general formulas I, II, III or IV $R^2$ is selected from hydrogen, halogen like fluorine, or $C_{1-4}$alkyl like $CH_3$ or $CF_3$, In another preferred embodiment of the compound according to the invention according to general formulas I, II, III or IV $R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl or $R^3$ is not alkyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl.

In another preferred embodiment of the compound according to the invention according to general formulas I, II, III or IV $R^3$ is selected from substituted or unsubstituted alkyl like propyl or butyl, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine.

In another preferred embodiment of the compound according to the invention according to general formulas I, II, III or IV $R^3$ is not alkyl. In such a preferred embodiment of the compound according to the invention according to general formulas I, II, III or IV $R^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine.

In another preferred embodiment of the compound according to the invention according to general formulas I, II, III or IV $R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl.

In another preferred embodiment of the compound according to the invention according to general formulas I, II, III or IV $R^4$ is selected from hydrogen or from substituted or unsubstituted $C_{1-4}$alkyl like $CH_3$ or $CH_2OH$.

In another preferred embodiment of the compound according to the invention according to general formulas I, II, III or IV $R^5$ is hydrogen, halogen, hydroxy, substituted or unsubstituted O-alkyl, substituted or unsubstituted alkyl, wherein the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the O-alkyl is —O—$C_{1-8}$alkyl like —Omethyl, —O-ethyl, —O-propyl, —O-butyl, —O-pentyl, —O-hexyl, —O-heptyl, or —O-octyl; preferably is —O—$C_{1-6}$alkyl like —O-methyl, —O-ethyl, —O-propyl, —O-butyl, —O-pentyl, or —O-hexyl; more preferably is —O—$C_{1-4}$alkyl like —O-methyl, —O-ethyl, —O-propyl or —O-butyl;
and/or
halogen is any of fluorine, chlorine, iodine or bromine, preferably chlorine or fluorine.

In another preferred embodiment of the compound according to the invention according to general formulas I, II, III or IV $R^5$ is selected from hydrogen or hydroxyl.

In another preferred embodiment of the compound according to the invention according to general formulas I, II, III or IV $R^6$, $R^7$, $R^8$ and $R^9$ are independent from each other and selected from the group formed by hydrogen, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl, and substituted or unsubstituted alkyl-aryl, or $R^6$ and $R^7$ or $R^8$ and $R^9$ together with their respective connecting carbon or nitrogen atom may form a cycloalkylic or heterocyclic 4 to 7-membered ring, wherein
  the aryl is phenyl, naphtyl or anthracene; preferably is napthyl and phenyl; more preferably is phenyl;
  and/or
  the alkyl-aryl is $C_{1-4}$-alkyl-aryl; preferably is benzyl;
  and/or
  the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;
  and/or
  the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;
  and/or
  the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;
  and/or
  the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;
  and/or
  the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;
  and/or
  when $R^6$ and $R^7$ or $R^8$ and $R^9$ together with their respective connecting carbon or nitrogen atom form a cycloalkylic or heterocyclic ring this ring is 5 or 6 membered, preferably $R^6$ and $R^7$ together with their respective connecting carbon atom form a saturated cycloalkylic ring of 5 or 6 members, more preferably $R^6$ and $R^7$ together with their respective connecting carbon atom form saturated, unsubstituted cyclohexyl;

In another preferred embodiment of the compound according to the invention according to general formulas I, II, III or IV $R^6$, $R^7$, $R^8$ and $R^9$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl, or $R^6$ and $R^7$ together with their connecting carbon atom form a cycloalkylic 5 or 6-membered ring like cyclohexyl.

In another preferred embodiment of the compound according to the invention according to general formulas I, II, III or IV
$V^1$ is selected from nitrogen or carbon;
m is 1 or 2;
n is 0 or 1;
$R^1$ is —$COR^6$, —$CONR^8R^9$, —$COCR^6R_7NR^8R^9$, substituted or unsubstituted alkyl like $C_{1-4}$-alkyl or $CH_3$, $C_2H_4OCH_3$, $C_3H_6OCH_3$;
$R^2$ is selected from hydrogen, halogen like fluorine, or $C_{1-4}$alkyl like $CH_3$ or $CF_3$;
$R^3$ is selected from substituted or unsubstituted alkyl like propyl or butyl, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;
$R^4$ is selected from hydrogen or from substituted or unsubstituted $C_{1-4}$alkyl like $CH_3$ or $CH_2OH$;
$R^5$ is selected from hydrogen or hydroxy; and
$R^6$, $R^7$, $R^8$ and $R^9$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl,
or $R^6$ and $R^7$ together with their connecting carbon atom may form a cycloalkylic 5 or 6-membered ring like unsubstituted cyclohexyl;

In another preferred embodiment of the compound according to the invention according to general formulas I, II, III or IV (wherein $R^3$ is not alkyl)
$V^1$ is selected from nitrogen or carbon;
m is 1 or 2;
n is 0 or 1;
$R^1$ is —$COR^6$, —$CONR^8R^9$, —$COCR^6R^7NR^8R^9$, substituted or unsubstituted alkyl like $C_{1-4}$-alkyl or $CH_3$, $C_2H_4OCH_3$, $C_3H_6OCH_3$;
$R^2$ is selected from hydrogen, halogen like fluorine, or $C_{1-4}$alkyl like $CH_3$ or $CF_3$;

R$^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;

R$^4$ is selected from hydrogen or from substituted or unsubstituted C$_{1-4}$alkyl like CH$_3$ or CH$_2$OH;

R$^5$ is selected from hydrogen or hydroxy; and

R$^6$, R$^7$, R$^8$ and R$^9$ are independently from each other selected from hydrogen, from substituted or unsubstituted C$_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl, or R$^6$ and R$^7$ together with their connecting carbon atom may form a cycloalkylic 5 or 6-membered ring like unsubstituted cyclohexyl.

In another preferred embodiment of the compound according to the invention according to general formulas I, II, III or IV the compound is having a general formula V,

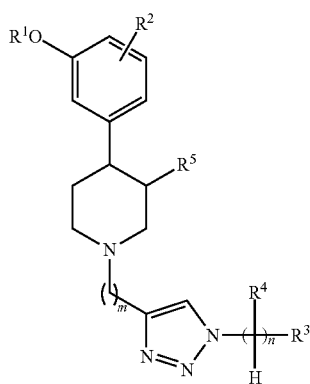

(V)

wherein m is 1 or 2, preferably is 1;

n is 0 or 1;

R$^1$ is —COR$^6$, —CONR$^8$R$^9$, —COCR$^6$R$^7$NR$^8$R$^9$, substituted or unsubstituted C$_{1-4}$alkyl, preferably is —COR$^6$, —CONR$^8$R$^9$, —COCR$^6$R$^7$NR$^8$R$^9$, —CH$_3$, —C$_2$H$_4$OCH$_3$, or —C$_3$H$_6$OCH$_3$;

R$^2$ is hydrogen, halogen, substituted or unsubstituted C$_{1-4}$alkyl, preferably is hydrogen;

R$^3$ is substituted or unsubstituted aryl or substituted or unsubstituted heterocyclyl, preferably is substituted or unsubstituted phenyl or substituted or unsubstituted pyridine;

R$^4$ is hydrogen, substituted or unsubstituted C$_{1-4}$alkyl, preferably is hydrogen or —CH$_2$OH;

R$^5$ is hydrogen, halogen or hydroxyl, preferably is hydrogen;

R$^6$, R$^7$, R$^8$ and R$^9$ are independent from each other and selected from the group formed by hydrogen, substituted or unsubstituted C$_{1-4}$alkyl, substituted or unsubstituted phenyl, substituted or unsubstituted heterocyclyl or substituted or unsubstituted benzyl, or R$^6$ and R$^7$ together with their connecting atom might form an unsubstituted 5- or 6-membered saturated cycloalkylic ring; preferably R$^6$, R$^7$, R$^8$ and R$^9$ are independent from each other selected from hydrogen, —CH$_3$, —CHCOOH, —C$_2$H$_5$, —C$_3$H$_7$, —CH(NH$_2$)C$_3$H$_7$, —CH(COOH)C$_3$H$_7$, substituted phenyl, unsubstituted pyrrolidine, unsubstituted benzyl, or R$^6$ and R$^7$ together with their connecting carbon atom form an unsubstituted cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a parallel preferred embodiment of the compound according to the invention according to general formulas I, II, III or IV the compound is having a general formula Va (which only differs from formula V by allowing V1 being also nitrogen),

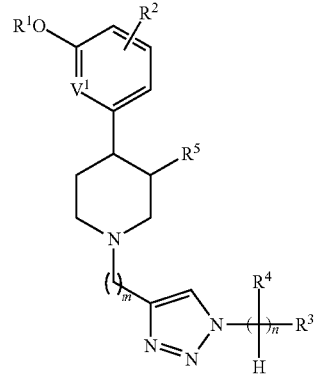

(Va)

wherein

V$^1$ is selected from nitrogen or carbon, preferably is carbon;

m is 1 or 2, preferably is 1;

n is 0 or 1;

R$^1$ is —COR$^6$, —CONR$^8$R$^9$, —COCR$^6$R$^7$NR$^8$R$^9$, substituted or unsubstituted C$_{1-4}$alkyl, preferably is —COR$^6$, —CONR$^8$R$^9$, —COCR$^6$R$^7$NR$^8$R$^9$, —CH$_3$, —C$_2$H$_4$OCH$_3$, or —C$_3$H$_6$OCH$_3$;

R$^2$ is hydrogen, halogen, substituted or unsubstituted C$_{1-4}$alkyl, preferably is hydrogen;

R$^3$ is substituted or unsubstituted aryl or substituted or unsubstituted heterocyclyl, preferably is substituted or unsubstituted phenyl or substituted or unsubstituted pyridine;

R$^4$ is hydrogen, substituted or unsubstituted C$_{1-4}$alkyl, preferably is hydrogen or —CH$_2$OH;

R$^5$ is hydrogen, halogen or hydroxyl, preferably is hydrogen;

R$^6$, R$^7$, R$^8$ and R$^9$ are independent from each other and selected from the group formed by hydrogen, substituted or unsubstituted C$_{1-4}$alkyl, substituted or unsubstituted phenyl, substituted or unsubstituted heterocyclyl or substituted or unsubstituted benzyl, or R$^6$ and R$^7$ together with their connecting atom might form an unsubstituted 5- or 6-membered saturated cycloalkylic ring; preferably R$^6$, R$^7$, R$^8$ and R$^9$ are independent from each other selected from hydrogen, —CH$_3$, —CHCOOH, —C$_2$H$_5$, —C$_3$H$_7$, —CH(NH$_2$)C$_3$H$_7$, —CH(COOH)C$_3$H$_7$, substituted phenyl, unsubstituted pyrrolidine, unsubstituted benzyl, or R$^6$ and R$^7$ together with their connecting carbon atom form an unsubstituted cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of a compound of general formula V (but also for formula Va with $V^1$ being selected from nitrogen or carbon) above m is 1;
and/or
n is 0 or 1;
and/or
$R^1$ is —$COR^6$, —$CONR^8R^9$, —$COCR^6R^7NR^8R^9$, —$CH_3$, —$C_2H_4OCH_3$, or —$C_3H_6OCH_3$;
and/or
$R^2$ is hydrogen;
and/or
$R^3$ is substituted or unsubstituted phenyl or substituted or unsubstituted pyridine;
and/or
$R^4$ is hydrogen or —$CH_2OH$;
and/or
$R^5$ is hydrogen;
and/or
$R^6$, $R^7$, $R^8$ and $R^9$ are independent from each other selected from hydrogen, —$CH_3$, —CHCOOH, —$C_2H_5$, —$C_3H_7$, —$CH(NH_2)C_3H_7$, —$CH(COOH)C_3H_7$, substituted phenyl, unsubstituted pyrrolidine, unsubstituted benzyl, or $R^6$ and $R^7$ together with their connecting carbon atom form an unsubstituted cyclohexyl.

In another preferred embodiment of a compound of general formula V above m is 1;
n is 0 or 1;
$R^1$ is —$COR^6$, —$CONR^8R^9$, —$COCR^6R^7NR^8R^9$, —$CH_3$, —$C_2H_4OCH_3$, or —$C_3H_6OCH_3$;
$R^2$ is hydrogen;
$R^3$ is substituted or unsubstituted phenyl or substituted or unsubstituted pyridine;
$R^4$ is hydrogen or —$CH_2OH$;
$R^5$ is hydrogen; and
$R^6$, $R^7$, $R^8$ and $R^9$ are independent from each other selected from hydrogen, —$CH_3$, —CHCOOH, —$C_2H_5$, —$C_3H_7$, —$CH(NH_2)C_3H_7$, —$CH(COOH)C_3H_7$, substituted phenyl, unsubstituted pyrrolidine, unsubstituted benzyl, or $R^6$ and $R^7$ together with their connecting carbon atom form an unsubstituted cyclohexyl.

In both these embodiment general formula V can be written as formula Va:

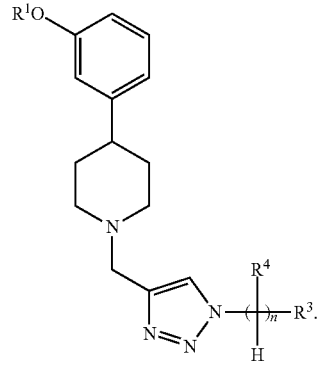

(Va)

In another preferred embodiment of the compound according to the invention according to general formulas I, II, III, IV and V (thus then applying to all definitions of all radicals $R^1$ to $R^9$ of the compounds of general formulas I, II, III, IV and V)

any aryl which is substituted is substituted by one or more of halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), any cycloalkyl or heterocyclyl which is substituted is substituted by one or more of halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br), and any alkyl, alkenyl, alkynyl or O-alkyl which is substituted is substituted by one or more of halogen (F, Cl, I, Br), —OH, —$NH_2$, —SH, —C(O)OH, or —$OC_{1-4}$alkyl being unsubstituted or substituted by one or more of OH or halogen (F, Cl, I, Br).

In another preferred embodiment of the compound according to the invention according to general formulas I, II, III, IV or V the compound is selected from 3-(1-((1-phenyl-1H-1,2,3-triazol-4-yl)methyl)piperidin-4-yl)phenyl ethylcarbamate,
1-((1-(4-fluorophenyl)-1H-1,2,3-triazol-4-yl)methyl)-4-(3-methoxyphenyl)piperidine,
3-(1-((1-(pyridin-2-ylmethyl)-1H-1,2,3-triazol-4-yl)methyl) piperidin-4-yl)phenyl acetate,
4-((3-(1-((1-(pyridin-2-ylmethyl)-1H-1,2,3-triazol-4-yl) methyl)piperidin-4-yl)phenylpyridin-2-ylmethyl)-1H-1, 2,3-triazol-4-yl)methyl)piperidin-4-yl)phenoxy)carbonylamino)benzoic acid,
3-(1-((1-(pyridin-2-ylmethyl)-1H-1,2,3-triazol-4-yl)methyl) piperidin-4-yl)phenyl isobutyrate,
(S)-3-(1-((1-(pyridin-2-ylmethyl)-1H-1,2,3-triazol-4-yl) methyl)piperidin-4-yl)phenyl 2-amino-3-methylbutanoate,
4-(3-methoxyphenyl)-1-((1-phenyl-1H-1,2,3-triazol-4-yl) methyl)piperidine,
3-(1-((1-phenyl-1H-1,2,3-triazol-4-yl)methyl)piperidin-4-yl)phenyl dimethylcarbamate,
3-(1-((1-phenyl-1H-1,2,3-triazol-4-yl)methyl)piperidin-4-yl)phenyl acetate,
4-(3-(2-methoxyethoxy)phenyl)-1-((1-phenyl-1H-1,2,3-triazol-4-yl)methyl)piperidine, 4-(3-(3-methoxypropoxy)phenyl)-1-((1-phenyl-1H-1,2,3-triazol-4-yl)methyl)piperidine,
2-((4-((4-(3-methoxyphenyl)piperidin-1-yl)methyl)-1H-1,2,3-triazol-1-yl)methyl)pyridine,
(S)-3-methyl-2-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)butanoic acid,
2-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)acetic acid,
3-fluoro-2-((4-((4-(3-methoxyphenyl)piperidin-1-yl)methyl)-1H-1,2,3-triazol-1-yl)methyl)pyridine,
5-fluoro-2-((4-((4-(3-methoxyphenyl)piperidin-1-yl)methyl)-1H-1,2,3-triazol-1-yl)methyl)pyridine,
2-(4-((4-(3-methoxyphenyl)piperidin-1-yl)methyl)-1H-1,2,3-triazol-1-yl)-2-phenylethanol,
(S)-3-(1-((1-(pyridin-2-ylmethyl)-1H-1,2,3-triazol-4-yl)methyl)piperidin-4-yl)phenyl pyrrolidine-2-carboxylate,
(S)-3-(1-((1-(pyridin-2-ylmethyl)-1H-1,2,3-triazol-4-yl)methyl)piperidin-4-yl)phenyl 2-amino-3-phenylpropanoate, and
3-(1-((1-(pyridin-2-ylmethyl)-1H-1,2,3-triazol-4-yl)methyl)piperidin-4-yl)phenyl 1-aminocyclohexanecarboxylate;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, IV or V the compound is selected from
3-(1-((1-phenyl-1H-1,2,3-triazol-4-yl)methyl)piperidin-4-yl)phenyl ethylcarbamate,
1-((1-(4-fluorophenyl)-1H-1,2,3-triazol-4-yl)methyl)-4-(3-methoxyphenyl)piperidine,
3-(1-((1-(pyridin-2-ylmethyl)-1H-1,2,3-triazol-4-yl)methyl)piperidin-4-yl)phenyl acetate,
4-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)benzoic acid,
3-(1-((1-(pyridin-2-ylmethyl)-1H-1,2,3-triazol-4-yl)methyl)piperidin-4-yl)phenyl isobutyrate,
(S)-3-(1-((1-(pyridin-2-ylmethyl)-1H-1,2,3-triazol-4-yl)methyl)piperidin-4-yl)phenyl 2-amino-3-methylbutanoate,
4-(3-methoxyphenyl)-1-((1-phenyl-1H-1,2,3-triazol-4-yl)methyl)piperidine,
3-(1-((1-phenyl-1H-1,2,3-triazol-4-yl)methyl)piperidin-4-yl)phenyl dimethylcarbamate,
3-(1-((1-phenyl-1H-1,2,3-triazol-4-yl)methyl)piperidin-4-yl)phenyl acetate,
4-(3-(2-methoxyethoxy)phenyl)-1-((1-phenyl-1H-1,2,3-triazol-4-yl)methyl)piperidine,
4-(3-(3-methoxypropoxy)phenyl)-1-((1-phenyl-1H-1,2,3-triazol-4-yl)methyl)piperidine,
2-((4-((4-(3-methoxyphenyl)piperidin-1-yl)methyl)-1H-1,2,3-triazol-1-yl)methyl)pyridine,
3-fluoro-2-((4-((4-(3-methoxyphenyl)piperidin-1-yl)methyl)-1H-1,2,3-triazol-1-yl)methyl)pyridine,
5-fluoro-2-((4-((4-(3-methoxyphenyl)piperidin-1-yl)methyl)-1H-1,2,3-triazol-1-yl)methyl)pyridine,
2-(4-((4-(3-methoxyphenyl)piperidin-1-yl)methyl)-1H-1,2,3-triazol-1-yl)-2-phenylethanol,
(S)-3-(1-((1-(pyridin-2-ylmethyl)-1H-1,2,3-triazol-4-yl)methyl)piperidin-4-yl)phenyl pyrrolidine-2-carboxylate,
(S)-3-(1-((1-(pyridin-2-ylmethyl)-1H-1,2,3-triazol-4-yl)methyl)piperidin-4-yl)phenyl 2-amino-3-phenylpropanoate, and
3-(1-((1-(pyridin-2-ylmethyl)-1H-1,2,3-triazol-4-yl)methyl)piperidin-4-yl)phenyl 1-aminocyclohexanecarboxylate;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment of the compound according to the invention according to general formulas I, II, III, IV or V the compound is selected from
3-(1-((1-phenyl-1H-1,2,3-triazol-4-yl)methyl)piperidin-4-yl)phenyl ethylcarbamate,
3-(1-((1-(pyridin-2-ylmethyl)-1H-1,2,3-triazol-4-yl)methyl)piperidin-4-yl)phenyl acetate,
4-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)benzoic acid,
3-(1-((1-(pyridin-2-ylmethyl)-1H-1,2,3-triazol-4-yl)methyl)piperidin-4-yl)phenyl isobutyrate,
(S)-3-(1-((1-(pyridin-2-ylmethyl)-1H-1,2,3-triazol-4-yl)methyl)piperidin-4-yl)phenyl 2-amino-3-methylbutanoate,
4-(3-methoxyphenyl)-1-((1-phenyl-1H-1,2,3-triazol-4-yl)methyl)piperidine,
3-(1-((1-phenyl-1H-1,2,3-triazol-4-yl)methyl)piperidin-4-yl)phenyl dimethylcarbamate,
3-(1-((1-phenyl-1H-1,2,3-triazol-4-yl)methyl)piperidin-4-yl)phenyl acetate,
4-(3-(2-methoxyethoxy)phenyl)-1-((1-phenyl-1H-1,2,3-triazol-4-yl)methyl)piperidine,
4-(3-(3-methoxypropoxy)phenyl)-1-((1-phenyl-1H-1,2,3-triazol-4-yl)methyl)piperidine,
(S)-3-(1-((1-(pyridin-2-ylmethyl)-1H-1,2,3-triazol-4-yl)methyl)piperidin-4-yl)phenyl pyrrolidine-2-carboxylate,
(S)-3-(1-((1-(pyridin-2-ylmethyl)-1H-1,2,3-triazol-4-yl)methyl)piperidin-4-yl)phenyl 2-amino-3-phenylpropanoate, and
3-(1-((1-(pyridin-2-ylmethyl)-1H-1,2,3-triazol-4-yl)methyl)piperidin-4-yl)phenyl 1-aminocyclohexanecarboxylate;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, IV or V the compound is selected from
3-(1-((1-phenyl-1H-1,2,3-triazol-4-yl)methyl)piperidin-4-yl)phenyl ethylcarbamate,
3-(1-((1-(pyridin-2-ylmethyl)-1H-1,2,3-triazol-4-yl)methyl)piperidin-4-yl)phenyl acetate,
4-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)benzoic acid,
3-(1-((1-(pyridin-2-ylmethyl)-1H-1,2,3-triazol-4-yl)methyl)piperidin-4-yl)phenyl isobutyrate, (S)-3-(1-((1-(pyridin-2-ylmethyl)-1H-1,2,3-triazol-4-yl)methyl)piperidin-4-yl)phenyl 2-amino-3-methylbutanoate, 4-(3-methoxyphenyl)-1-((1-phenyl-1H-1,2,3-triazol-4-yl)methyl)piperidine, 3-(1-((1-phenyl-1H-1,2,3-triazol-4-yl)methyl)piperidin-4-yl)phenyl dimethylcarbamate, 3-(1-((1-phenyl-1H-1,2,3-triazol-4-yl)methyl)piperidin-4-yl)phenyl acetate, 4-(3-(2-methoxyethoxy)phenyl)-1-((1-phenyl-1H-1,2,3-triazol-4-yl)methyl)piperidine, 4-(3-(3-methoxypropoxy)phenyl)-1-((1-phenyl-1H-1,2,3-triazol-4-yl)methyl)piperidine, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another highly preferred embodiment of the compound according to the invention according to general formulas I, II, III, IV or V the compound is selected from 3-(1-((1-phenyl-1H-1,2,3-triazol-4-yl)methyl)piperidin-4-yl)phenyl acetate, and 3-(1-((1-(pyridin-2-ylmethyl)-1H-1,2,3-triazol-4-yl)methyl)piperidin-4-yl)phenyl acetate;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the σ1 receptor and the μ-opiod receptor it is a very preferred embodiment in which the compounds are selected which act as dual ligands of the σ1 receptor and the μ-opiod receptor and especially compounds which have a binding expressed as $K_i$ which is <100 nm for both receptors.

In the following the phrase "compound of the invention" is used. This is to be understood as any compound according to the invention as described above according to general formulas I, II, III, IV, or V.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to formula I,

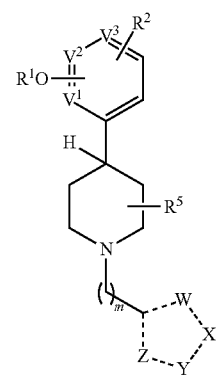

wherein $R^1$, $R^2$, $R^5$, $V^1$, $V^2$, $V^3$, W, X, Y, Z and m are as defined for formula (I) or for a compound according to formula Ia (below)

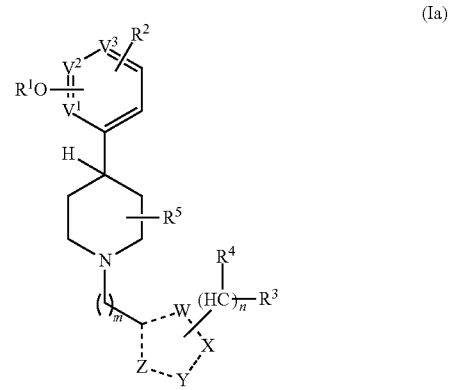

(Ia)

wherein $R^1$, $R^2$, $R^3$, $R^4$, $R^5$, $V^1$, $V^2$, $V^3$, W, X, Y, Z, n and m are as defined for formula I, wherein a compound of formula X or its suitable salt like the hydrochloride

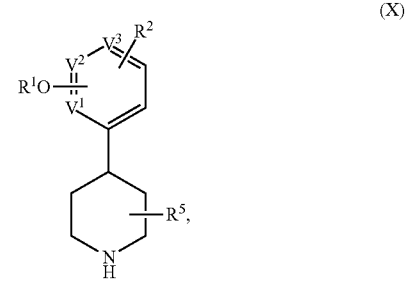

(X)

wherein $R^1$, $R^2$, $R^5$, $V^1$, $V^2$, and $V^3$ are as defined for formula I, is reacted with a compound according to formula XI (for a compound according to formula I) or according to formula XIa (for a compound according to formula Ia) under the conditions of Step 1

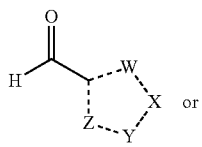 (XI)

or

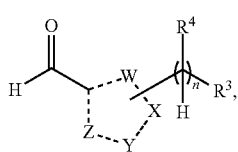 (XIa)

wherein $R^3$, $R^4$, W, X, Y, Z and n are as defined for formula I, leading to a compound according to formula (I) or formula (Ia) respectively, wherein the reductive amination reaction of the compounds of formula (X) and (XI or XIa) of Step 1 is carried out with a reductive reagent in an aprotic solvent in the presence of an organic base.

Preferably in the reaction of Step 1 above the reductive reagent is sodium triacetoxyborohydride, the aprotic solvent is dichloroethane and/or the organic base is diisopropylethylamine.

Another preferred aspect of the invention is a process for the production of a compound according to the invention, wherein a the compound is a compound of formula V

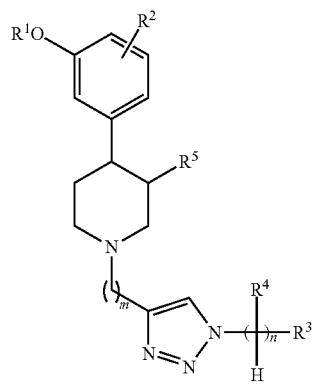 (V)

or a compound according to claim 1 according to formula I with

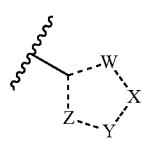

being

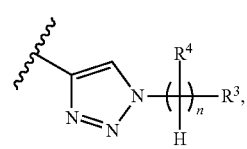

wherein $R^1$, $R^2$, $R^3$, $R^4$, $R^5$, $V^1$, $V^2$, $V^3$, W, X, Y, Z, n and m are as defined for formula V or formula I, respectively, wherein a compound of formula VI or its suitable salt like the hydrochloride

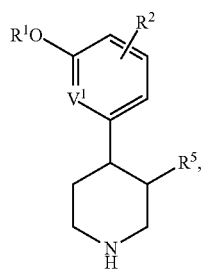 (VI)

wherein $R^1$, $R^2$, $R^5$ and $V^1$ are as defined for formula V or formula I, respectively, is reacted with a compound according to formula VIII under the conditions of Step 2

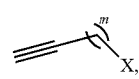 (VIII)

wherein m is as defined for formula V or formula I, leading to a compound according to formula VII,

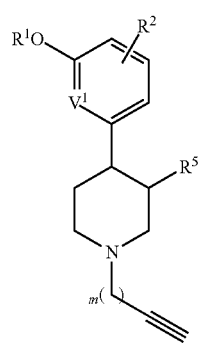 (VII)

wherein $R^1$, $R^2$, $R^5$, $V^1$ and m are as defined for formula V or formula I, respectively.

Preferably this is followed by reacting said compound according to formula VII with a compound according to formula IX under the conditions of Step 3

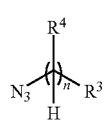 (IX)

wherein $R^3$, $R^4$ and n are as defined for formula V or formula I, respectively, under the conditions of Step 3, leading to a compound according to formula (V), wherein X is a leaving group like a halogen or sulphate like chlorine, wherein the reaction of Step 2 of said compounds of general formula (VI) with said compounds of formula (VIII) is carried out in the presence of a base in an aprotic solvent;

wherein the reaction of Step 3 of said compounds of general formula (VII) with said compounds of formula (IX) is carried out in the presence of a copper salt and sodium ascorbate in a mixture of protic organic solvent and water.

Preferably in the reaction of Step 2 above the base is Et$_3$N, the aprotic solvent is tetrahydrofurane (THF) and/or the reaction is preferably carried out at a temperature range of 25-75° C. The temperature may be raised by conventional methods or by use of microwave.

Preferably in the reaction of Step 3 above the copper salt is CuSO$_4$.5H$_2$O and the mixture of protic organic solvent and water is a mixture of t-BuOH:H$_2$O 1:1 and/or the reaction is preferably carried out at room temperature.

Another preferred aspect of the invention is a process for the production of a compound according to the invention, wherein the compound is a compound of formula V

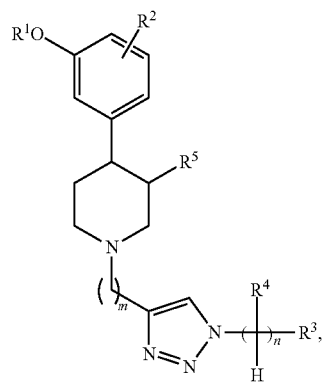

(V)

wherein R$^1$, R$^2$, R$^3$, R$^4$, R$^5$, n and m are as defined for formula V above, wherein a compound of formula VI or its suitable salt like the hydrochloride

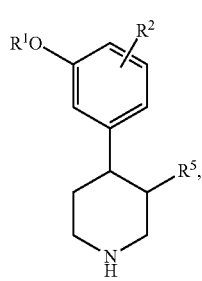

(VI)

wherein R$^1$, R$^2$, and R$^5$ are as defined for formula V above, is reacted with a compound according to formula VIII under the conditions of Step 2

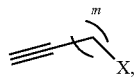

(VIII)

wherein m is as defined for formula V above, leading to a compound according to formula VII,

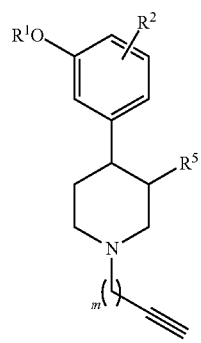

(VII)

wherein R$^1$, R$^2$, R$^5$ and m are as defined for formula V above.

Preferably this is followed by reacting said compound according to formula VII with a compound according to formula IX under the conditions of Step 3

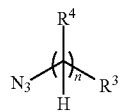

(IX)

wherein R$^3$, R$^4$ and n are as defined for formula V above, under the conditions of Step 3, leading to a compound according to formula (V), wherein X is a leaving group like a halogen or sulphate like chlorine, wherein the reaction of Step 2 of said compounds of general formula (VI) with said compounds of formula (VIII) is carried out in the presence of a base in an aprotic solvent;

wherein the reaction of Step 3 of said compounds of general formula (VII) with said compounds of formula (IX) is carried out in the presence of a copper salt and sodium ascorbate in a mixture of protic organic solvent and water.

Preferably in the reaction of Step 2 above the base is Et$_3$N, the aprotic solvent is tetrahydrofurane (THF) and/or the reaction is preferably carried out at a temperature range of 25-75° C. The temperature may be raised by conventional methods or by use of microwave.

Preferably in the reaction of Step 3 above the copper salt is CuSO$_4$.5H$_2$O and the mixture of protic organic solvent and water is a mixture of t-BuOH:H$_2$O 1:1 and/or the reaction is preferably carried out at room temperature.

In summary, this gives the following Scheme:

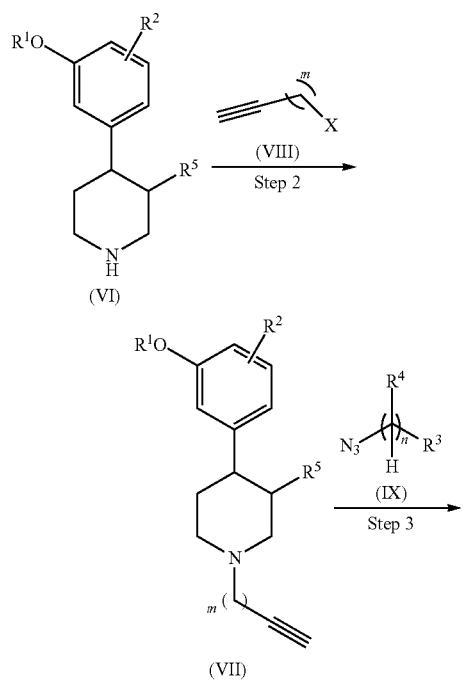

Another preferred aspect of the invention is a process for the production of a compound according to the invention, wherein the compound is a compound of formula Ib

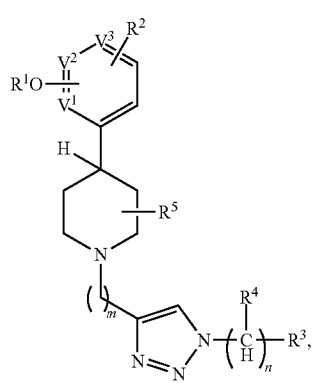

wherein $R^1$, $R^2$, $R^3$, $R^4$, $R^5$, $V^1$, $V^2$, $V^3$, n and m are as defined for formula Ib, wherein a compound of formula VIa or its suitable salt like the hydrochloride

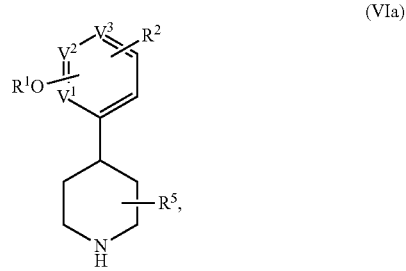

wherein $R^1$, $R^2$, $R^5$, $V^1$, $V^2$ and $V^3$ are as defined for formula Ib, is reacted with a compound according to formula VIII under the conditions of Step 2

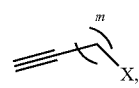

wherein m is 1 or 2, leading to a compound according to formula VIIa,

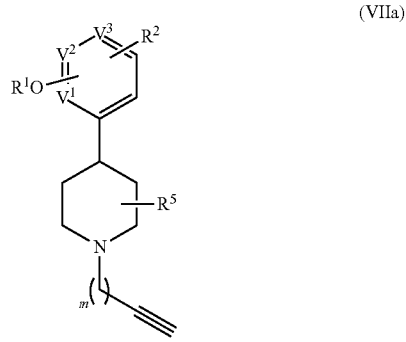

wherein $R^1$, $R^2$, $R^5$, $V^1$, $V^2$, $V^3$ and m are as defined for formula Ib.

Preferably this is followed by reacting said compound according to formula VIIa with a compound according to formula IX under the conditions of Step 3

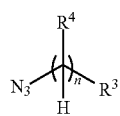

(IX)

wherein $R^3$, $R^4$ and n are as defined as for formula Ib, under the conditions of Step 3, leading to a compound according to formula Ib, wherein X is a leaving group like a halogen or sulphate like chlorine, wherein the reaction of Step 2 of said compounds of general formula (VIa) with said compounds of formula (VIII) is carried out in the presence of a base in an aprotic solvent;

wherein the reaction of Step 3 of said compounds of general formula (VIIa) with said compounds of formula (IX) is carried out in the presence of a copper salt and sodium ascorbate in a mixture of protic organic solvent and water.

Preferably in the reaction of Step 2 above the base is Et$_3$N, the aprotic solvent is tetrahydrofurane (THF) and/or the reaction is preferably carried out at a temperature range of 25-75° C. The temperature may be raised by conventional methods or by use of microwave.

Preferably in the reaction of Step 3 above the copper salt is CuSO$_4$.5H$_2$O and the mixture of protic organic solvent and water is a mixture of t-BuOH:H$_2$O 1:1 and/or the reaction is preferably carried out at room temperature.

In summary, this gives the following Scheme:

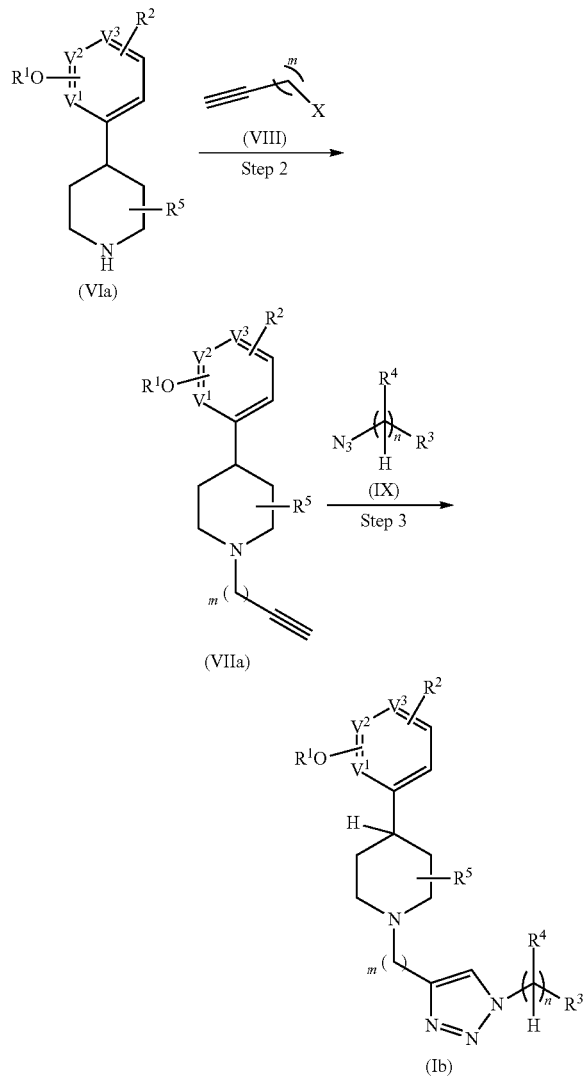

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, II, III, IV, or V or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formulas I, II, III, IV, or V or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis All solvents used for synthesis were p. a. quality.
Method I A process is described for the preparation of compounds of general formula ($I_{ex}$) where $R_1$, $R_2$, $R_3$, $R_4$, $R_5$, A, B, C, D, W, n and m have the meanings as defined above (with "A", "B", "C", and "D" being "X", "Y", "Z", "W" in the above description, respectively, and "W" being "$V^1$" in the above description), comprising the reaction of compound of formula ($II_{ex}$), or its suitable salt, such as hydrochloride, with a compound of general formula ($III_{ex}$) as described in scheme 1:

Scheme 1:

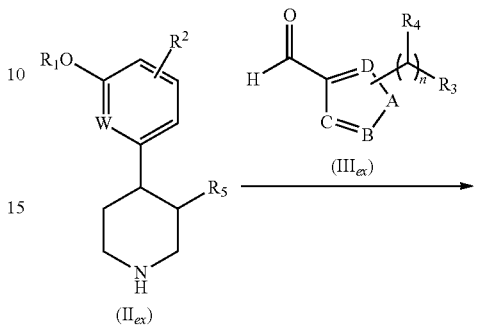

The reductive amination reaction of compounds of formula ($II_{ex}$) and ($III_{ex}$) is preferably carried out with a reductive reagent, preferably sodium triacetoxyborohydride, in an aprotic solvent, preferably dichloroethane, in the presence of an organic base, preferably diisopropylethylamine.

Method II

A process is described for the preparation of compounds of general formula ($Ia_{ex}$ and $Ib_{ex}$) where $R_1$, $R_2$, $R_3$, $R_4$, $R_5$, W, n and m have the meanings as defined above (with "W" being "$V^1$" in the above description), comprising the reaction of a compound of formula ($II_{ex}$) with a compound of formula ($IV_{ex}$), where X is a suitable leaving group such as a halogen or sulfonate, and the reaction of the resulting intermediate ($V_{ex}$) with convenient reagents such as ($VI_{ex}$), ($VII_{ex}$) or ($VIII_{ex}$) to give the triazoles ($Ia_{ex}$) and ($Ib_{ex}$). As indicated in Scheme 2 different methods can be used in the practical realization of these two reactions. In some cases, the intermediate ($V_{ex}$) can be isolated but in other cases the two steps may be carried out one-pot. The compounds of formula ($IV_{ex}$) and the reagents of formula ($VI_{ex}$), ($VII_{ex}$) or ($VIII_{ex}$) are either commercially available or can be prepared following conventional methods reported in the literature. Alternately, some of the azides can be prepared in situ.

Scheme 2:

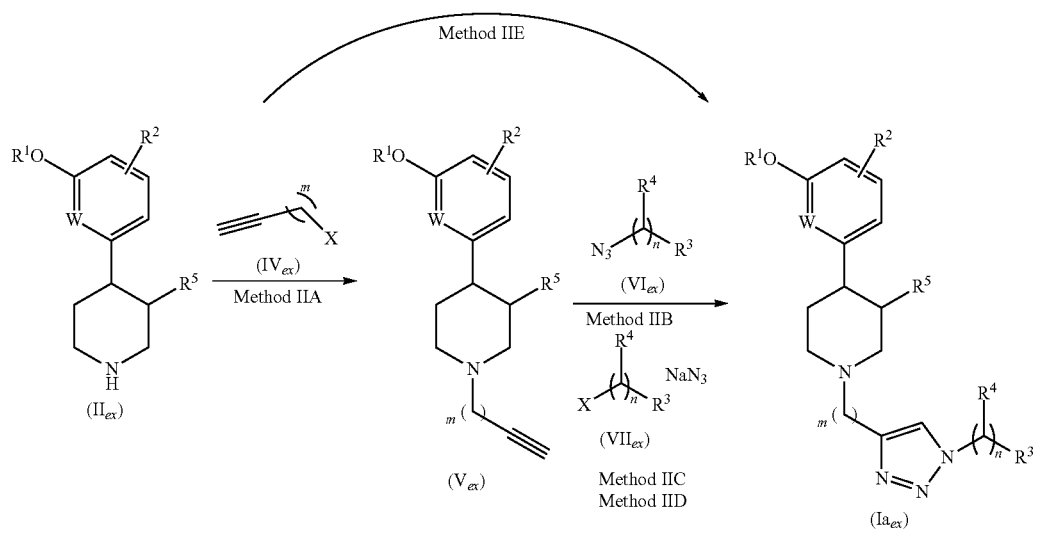

In Method IIA the reaction of compounds of general formula ($II_{ex}$) with compounds of formula ($IV_{ex}$) where X is a suitable leaving group, such as halogen or sulfonate, is carried out in the presence of a base, preferably $Et_3N$, in an aprotic solvent such as tetrahydrofurane (THF) at a temperature range of 25-75° C., using conventional heating or a microwave reactor.

In Method IIB the reaction of compounds of formula ($V_{ex}$) with azides of general formula ($VI_{ex}$) is carried out in the presence of a copper salt, preferably $CuSO_4.5H_2O$ and sodium ascorbate, in a mixture of protic organic solvent and water, preferably a mixture of t-BuOH:$H_2O$ 1:1 at room temperature.

In Method IIC the azide is generated in situ. The precursor of the azide ($VII_{ex}$), where X is a suitable leaving group such as halogen or sulfonate, is treated with sodium azide and a copper salt, preferably CuI, in an organic solvent, preferably dimethylformamide, at 100° C. using microwave irradiation. Alternatively, some additives such as $N_1,N_2$-dimethylethane-1,2-diamine (DMEDA) and sodium ascorbate can be added to the reaction mixture.

In Method IID the precursor of the azide of general formula ($VII_{ex}$) is treated with sodium azide in a mixture of a protic organic solvent and water, preferably a mixture of t-BuOH:$H_2O$ 1:1, at 100° C. using microwave irradiation for a suitable time, such as 1 h or until completed reaction. The in situ formed azide is then treated with compounds of general formula ($V_{ex}$) in the presence of a copper salt, preferably $CuSO_4.5H_2O$ and sodium ascorbate at room temperature.

In Method IIE the intermediates of general formula ($Ia_{ex}$) are prepared in a one-pot procedure comprising the reaction of compounds of general formula ($II_{ex}$) and propargyl bromide in the presence of a base, preferably $Et_3N$, in water at room temperature for 1 h or until completed reaction, after which compounds of general formula ($VI_{ex}$) are added in the presence of a copper salt, preferably CuI, at room temperature (*Tetrahedron* 2005, 61, 9331-9337).

If desired, racemic intermediates of general formula ($II_{ex}$) or final compounds of general formula ($I_{ex}$) may be resolved into their enantiomers by conventional resolution methods as for example, chiral chromatography, crystallization of the diastereomeric salts, etc.

Thus, the obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Method III

Scheme 3:

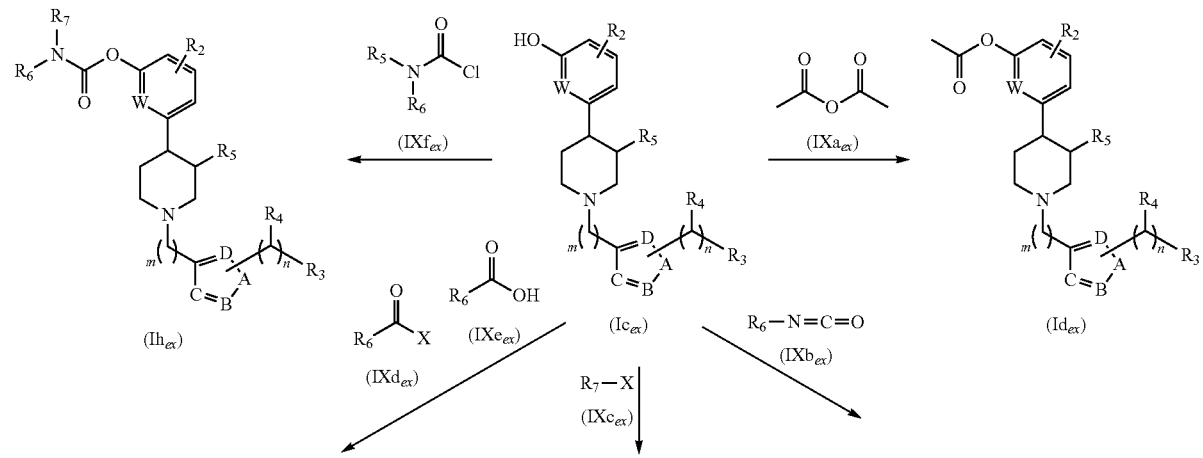

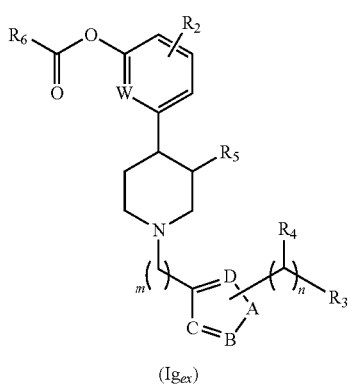
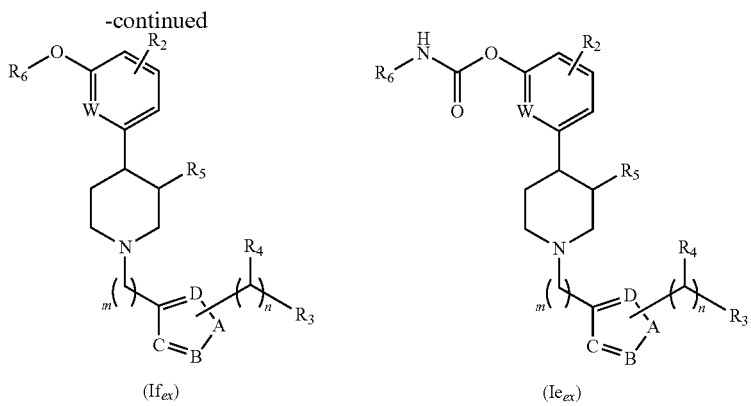

The process for the preparation of intermediates of formula ($Id_{ex}$-$h_{ex}$) where $R_2$, $R_3$, $R_4$, $R_5$, $R_6$, $R_7$, A, B, C, D, W, m and n have the meanings as defined above (with "A", "B", "C", and "D" being "X", "Y", "Z", "W" in the above description, respectively, and "W" being "V$^1$" in the above description), according to scheme 3, which comprises the reaction of compounds of formula ($Ic_{ex}$) with a compound of formula ($IXa_{ex}$-$d_{ex}$), where X is a suitable leaving group such as halogen, in the presence of a base, preferably pyridine, $Et_3N$, NaH, $K_2CO_3$ or $Cs_2CO_3$, alternatively in the presence of 4-N,N-dimethylaminopyridine, at a range of temperature of 0 to 120° C., in the presence of a suitable solvent, such as dichloromethane, acetone, acetonitrile or THF; alternatively, the reactions can be carried out in a microwave reactor.

Alternatively, compounds ($Ig_{ex}$) can be prepared by reaction of compounds ($Ic_{ex}$) with a carboxylic acid of formula ($IXe_{ex}$) in the presence of an activating agent, preferably N-Ethyl-N'-(3-dimethylaminopropyl)carbodiimide hydrochloride (EDAC-HCl), and 4-dimethylaminopyridine as additive, in an organic solvent, preferably dichloromethane.

In some cases, an additional final deprotection step was needed to obtain compounds of formula ($Ie_{ex}$) and ($Ig_{ex}$), preferably in an acidic medium, preferably HCl in an organic solvent, preferably 1,4-dioxane, or trifluoroacetic acid.

Synthesis of Intermediates of General Formula ($II_{ex}$)

In some cases, compounds of formula ($II_{ex}$) are commercially available or they can be obtained by conventional methods. Alternatively compound of formula ($II_{ex}$) can be obtained following different methods:

Method IV

Scheme 4

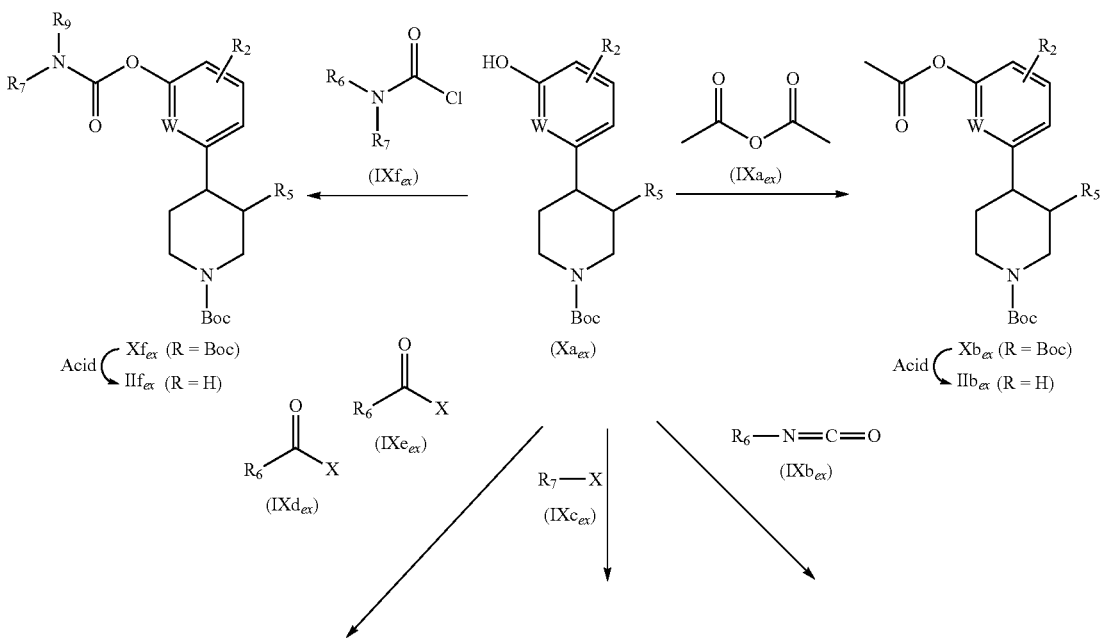

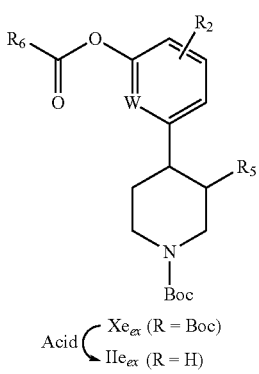 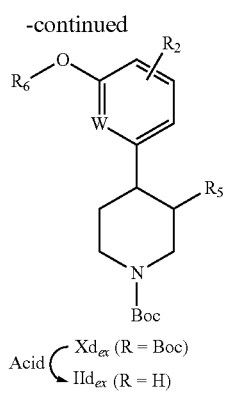 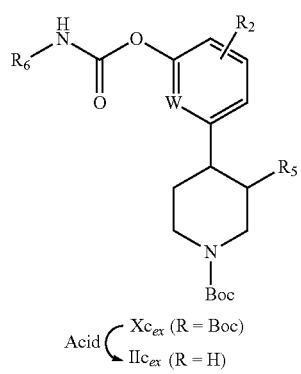

The process for the preparation of intermediates of general formula (IIb$_{ex}$-f$_{ex}$) where W, R$_2$, R$_5$, R$_6$, R$_7$, have the meanings as defined above (with "A", "B", "C", and "D" being "X", "Y", "Z", "W" in the above description, respectively, and "W" being "V$^1$" in the above description), according to the reaction sequence shown in scheme 4, which comprises:

a) The reaction of compounds of formula (Xa$_{ex}$) with a compound of formula (IXa$_{ex}$-d$_{ex}$ and f$_{ex}$), where X is a suitable leaving group, such as halogen, in the presence of a base, preferably pyridine, Et$_3$N, NaH, K$_2$CO$_3$ or CS$_2$CO$_3$, alternatively in the presence of 4-N,N-dimethylaminopyridine, at a range of temperature of 0 to 120° C., in the presence of a suitable solvent, such as dichloromethane, toluene, acetone, acetonitrile, THF or DMF; alternatively, the reactions can be carried out in a microwave reactor. Alternatively, compounds (IIe$_{ex}$) can be prepared by reaction of compounds (Xa$_{ex}$) with a carboxylic acid of formula (IXe$_{ex}$) in the presence of an activating agent, preferably N-Ethyl-N'-(3-dimethylaminopropyl)carbodiimide hydrochloride (EDAC-HCl), and 4-dimethylaminopyridine as additive, in an organic solvent, preferably dichloromethane b) The deprotection of the resulting compounds (Xb$_{ex}$-f$_{ex}$) in an acidic medium, preferably HCl in an organic solvent, preferably 1,4-dioxane.

Method V

Scheme 5

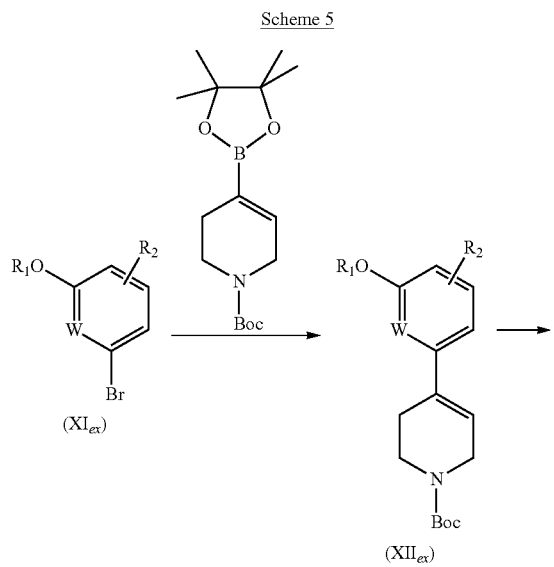

The process for the preparation of intermediates of general formula (IIg$_{ex}$) where W, R$_1$ and R$_2$ have the meanings as defined above (with W being V$^1$ above), according to the reaction sequence shown in scheme 5 and comprises:

a) The coupling reaction of an aromatic bromide of general formula (XI$_{ex}$) with 3,6-dihydro-2H-pyridine-1-tert-butoxycarbonyl-4-boronic acid pinacol ester in the presence of a palladium catalyst, such as Pd(PPh$_3$)$_4$ and an inorganic base, preferably K$_2$CO$_3$ or Na$_2$CO$_3$ in a mixture of organic solvents and water, preferably a mixture of dimethoxyethane/ethanol/water or dioxane/ethanol/water at a temperature range of 90-160° C. Alternatively, the reaction can be carried out in a microwave reactor. The bromides of general formula (XI$_{ex}$) are commercially available or can be prepared by conventional methods.

b) The reduction of compounds of formula (XII$_{ex}$), by any suitable method such as hydrogenation using a palladium catalyst, preferably Pd(OH)$_2$, in a protic solvent preferably MeOH.

c) The deprotection of the resulting compounds of formula (XII$_{ex}$) in an acidic medium, preferably HCl in an organic solvent preferably 1,4-dioxane.

Synthesis of Intermediates of General Formula III$_{ex}$

The aldehydes of general formula (III$_{ex}$) where R$_3$, R$_4$, A, B, C, D and n have the meanings as defined above (with "A", "B", "C", and "D" being "X", "Y", "Z", "W" in the above description, respectively), are commercially available or can be prepared by methods described in the bibliography (for example, WO2010046780 A2, WO2008157844 A1) or by the methods described below and summarized in Scheme 6.

Scheme 6

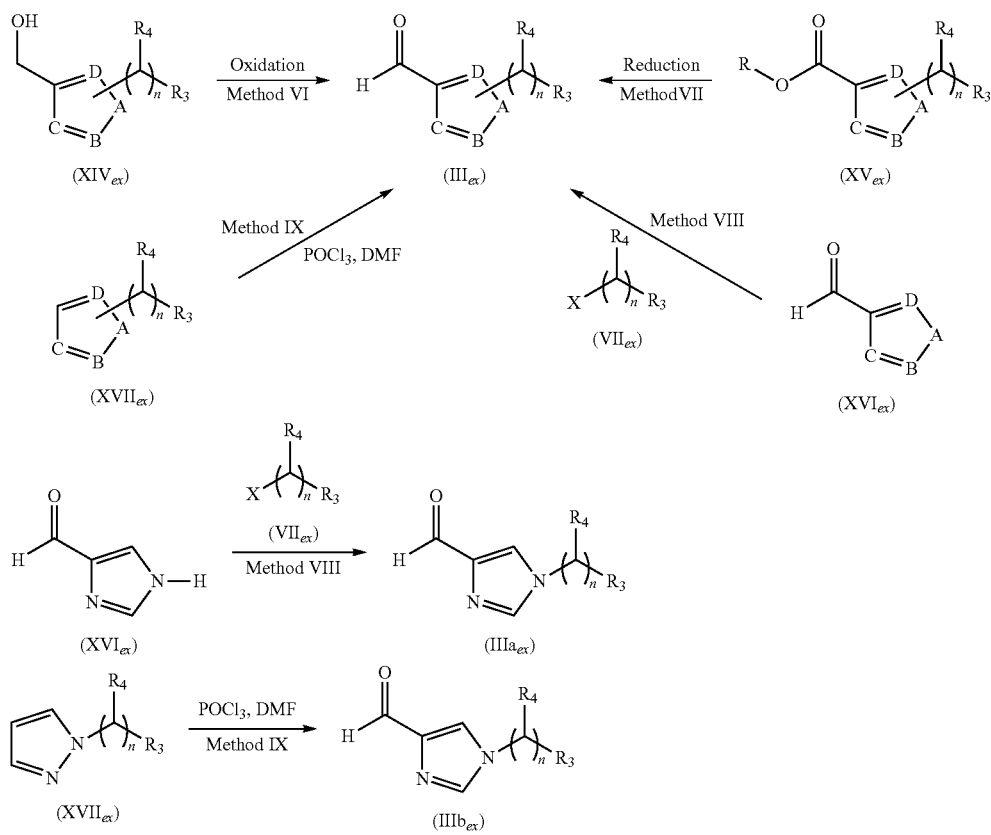

Method VI involves the oxidation of compounds of general formula (XIV$_{ex}$), using a suitable oxidizing reagent, such as MnO$_2$, in an aprotic solvent such as dichloromethane.

Method VII involves the reduction of compounds of general formula (XV$_{ex}$) with a suitable reducing agent such as DIBAL-H at −78° C. in an aprotic solvent, preferably dichloromethane.

Method VIII, which is exemplified for the preparation of compounds of formula (IIIa$_{ex}$), comprises the reaction between compounds of formula (XVI$_{ex}$) with compounds of general formula (VII$_{ex}$) where X is a suitable leaving group as halogen or sulfonate, in the presence of an inorganic base, preferably an aqueous solution of NaOH and a phase transfer catalyst, preferably tetra-n-butylammonium bromide, in an aprotic solvent preferably toluene at room temperature.

Method IX, which is exemplified for the preparation of compounds of formula (IIIb$_{ex}$), comprises the reaction between the compounds of general formula (XVII$_{ex}$) with POCl$_3$ in DMF as solvent at 90-110° C.

Synthesis of Intermediates of General Formula XIV$_{ex}$

The alcohols of general formula (XIV$_{ex}$) where R$_3$, R$_4$, A, B, C, D and n have the meanings as defined above, are commercially available or can be prepared by methods described in the bibliography (for example *J. Org. Chem.* 2010, 75, 6540-6548, WO2010080864, *Org. Lett.* 2009, 21, 4954-4957, *J. Med. Chem.* 2011, 54, 5988-5999). In particular, alcohols of formula XIVa$_{ex}$ and XIVb$_{ex}$ can be prepared by the methods outlined in Scheme 7.

Scheme 7

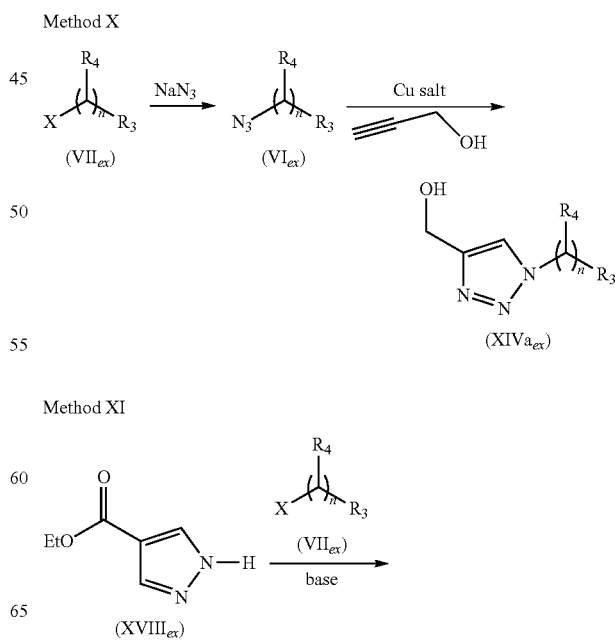

Method XII

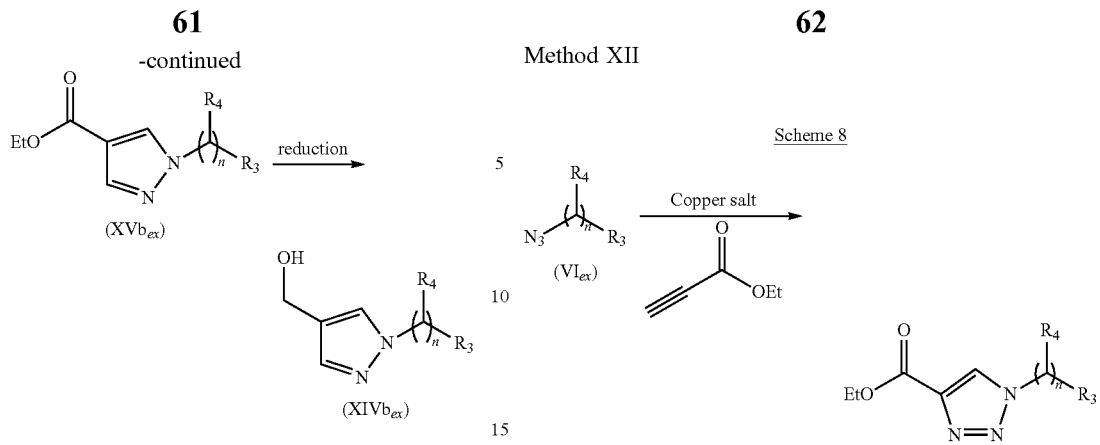

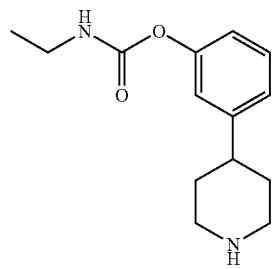 [SMILES: CCNC(=O)Oc1cccc(C2CCNCC2)c1]

Method X comprises the cycloaddition reaction of an azide of general formula (VI$_{ex}$) with propargyl alcohol in the presence of a copper salt as catalys. The azides of general formula (VI$_{ex}$) are commercially available or may be prepared following conventional methods reported in the literature; alternately, some of the azides can be prepared in situ. The reaction is performed in the presence of a copper salt, preferably CuSO$_4$.5H$_2$O and sodium ascorbate in a mixture of protic organic solvent and water, preferably a mixture of t-BuOH:H$_2$O 1:1 at room temperature Alternatively, CuI can be used as copper salt in a polar solvent as dimethylformamide at 100° C. using microwave irradiation or Cu(OAc)$_2$ can be used as copper salt in a polar solvent, such as methanol at room temperature. The reaction can also be effected using a one-pot procedure, in which case it is performed with sodium azide in a mixture of protic organic solvent and water, preferably a mixture of t-BuOH:H$_2$O 1:1, heating at 100° C. using microwave irradiation for 1 h or until completed reaction, followed by the reaction with propargyl alcohol in the presence of a copper salt, preferably CuSO$_4$.5H$_2$O and sodium ascorbate at room temperature. Alternatively, CuI is used as copper salt in a polar solvent, such as dimethylformamide and at 90° C. using microwave irradiation.

Compounds of general formula (XIVb$_{ex}$), where R$_3$, R$_4$, and n have the meanings as defined above can be prepared using Method XI. This process comprises:
a) The reaction between compound of formula (XVIII$_{ex}$) with a compound of general formula (VII$_{ex}$) where X is a suitable leaving group such as halogen or sulfonate, in the presence of a base, preferably K$_2$CO$_3$, in a polar solvent, preferably acetone at 60° C.
b) The reduction of the resulting compound (XVb$_{ex}$) with a suitable hydride reagent, preferably LiAlH$_4$ at 0° C., in an aprotic solvent, preferably THF.

Synthesis of Intermediates of General Formula XV$_{ex}$

The esters of general formula (XV$_{ex}$), where R$_3$, R$_4$, A, B, C, D and n have the meanings as defined above, are commercially available or can be prepared by methods described in the bibliography (*Synthesis*, 1975, 9, 609-610; WO2011098904; *Org. Lett.* 2010, 12, 9, 2166-2169)

The esters of general formula (XVa$_{ex}$), where R$_3$, R$_4$, and n have the meanings as defined above, can be prepared by Method XII, which involves the cycloaddition reaction of an azide of general formula (VI$_{ex}$) with ethyl propiolate in the presence of a copper salt as catalyst, preferably Cu(OTf)$_2$.C$_6$H$_6$ in an aprotic solvent, preferably toluene, at 70-100° C. (Scheme 8).

SYNTHESIS OF INTERMEDIATES

Example of Preparation of an Intermediate of Formula (IICe), Method IV

Synthesis of 3-(piperidin-4-yl)phenyl ethylcarbamate tert-Butyl 4-(3-((ethylcarbamoyl)oxy)phenyl)piperidine-1-carboxylate: To a solution of tert-butyl 4-(3-hydroxyphenyl)piperidine-1-carboxylate (60 mg, 0.21 mmol) in toluene (4 mL), ethylisocyanate (34 μl, 0.43 mmol) and pyridine (7 μl, 0.087 mmol) were added. The mixture was heated at 110° C. overnight. The reaction mixture was cooled, ethyl acetate was added and the reaction mixture was washed with water, brine, dried over Na$_2$SO$_4$ and concentrated under vacuum. The residue was purified by flash chromatography, silica gel, gradient hexane to ethyl acetate to afford the title compound (47 mg, 62% yield). $^1$H-NMR (300 MHz, CDCl$_3$), δ ppm: 7.29 (t, J=8 Hz, 1H), 7.04 (t, J=8 Hz, 1H), 6.98 (m, 2H), 5.04 (bs, 1H), 3.33 (m, 2H), 2.79 (m, 2H), 2.65 (tt J=12, 3.5 Hz, 1H), 1.84 (m, 2H), 1.63 (m, 4H), 1.49 (s, 9H), 1.23 (t, J=7 Hz, 3H).

3-(Piperidin-4-yl)phenyl ethylcarbamate: To a solution of tert-butyl 4-(3-((ethylcarbamoyl)oxy)phenyl)piperidine-1-carboxylate (47 mg, 0.13 mmol) in dioxane (0.5 mL), a solution of 4M HCl in dioxane (0.5 mL, 2.02 mmol) was added and the mixture was stirred at rt overnight. The solution was concentrated to dryness to afford the title compound (38 mg, 99% yield) as hydrochloride. $^1$H-NMR (500 MHz, MeOD), δ ppm: 7.35 (t, J=8 Hz, 1H), 7.14 (t, J=8 Hz, 1H), 7.04 (s, 1H), 6.99 (d, J=8 Hz, 1H), 3.68 (m, 1H), 3.50 (m, 2H), 3.22 (q, J=7 Hz, 2H), 3.14 (m, 2H), 2.93 (m, 1H), 2.07 (m, 2H), 1.94 (m, 2H), 1.19 (t, J=7 Hz, 3H).

Example of Preparation of an Intermediate of Formula (IId$_{ex}$), Method IV

Synthesis of 4-(3-(2-methoxyethoxy)phenyl)piperidine

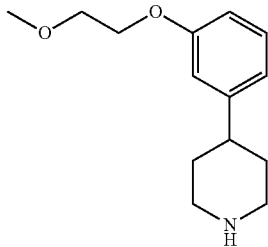 [SMILES: COCCOc1cccc(C2CCNCC2)c1]

tert-Butyl 4-(3-(2-methoxyethoxy)phenyl)piperidine-1-carboxylate: In a microwave vial, to a solution of tert-butyl 4-(3-hydroxyphenyl)piperidine-1-carboxylate (80 mg, 0.28 mmol) and Cs$_2$CO$_3$ (188 mg, 0.57 mmol) in acetonitrile (3 mL), 1-bromo-2-methoxyethane (80 mg, 0.57 mmol) was added and the mixture was irradiated with microwaves at 100° C. for 30 min. Water was added and the product was extracted with ethyl acetate, the organic phase was washed with brine, dried Na$_2$SO$_4$, filtered and concentrated under vacuum to afford the title product (80 mg, 83% yield). $^1$H-NMR (400 MHz, CDCl$_3$), δ ppm: 7.23 (t, J=8 Hz, 1H), 6.81 (m, 3H), 4.24 (m, 2H), 4.13 (m, 2H), 3.77 (m, 2H), 3.47 (s, 3H), 2.80 (m, 2H), 2.62 (tt J=12, 3.5 Hz, 1H), 1.83 (m, 2H), 1.63 (m, 2H), 1.50 (s, 9H).

4-(3-(2-Methoxyethoxy)phenyl)piperidine: To a solution of tert-Butyl 4-(3-(2-methoxyethoxy)phenyl)piperidine-1-carboxylate (80 mg, 0.23 mmol) in dioxane (0.5 mL), a solution of 4M HCl in dioxane (0.89 mL, 3.5 mmol) was added and stirred at rt overnight. The mixture was concentrated to dryness to afford the titled compound (60 mg, 95% yield) as hydrochloride that was used directly in the next step.

Example of Preparation of an Intermediate of Formula (IIf$_{ex}$), Method IV

Synthesis of 3-(piperidin-4-yl)phenyl dimethylcarbamate

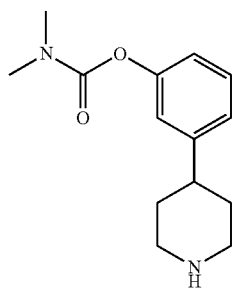 [SMILES: CN(C)C(=O)Oc1cccc(C2CCNCC2)c1]

tert-Butyl 4-(3-((dimethylcarbamoyl)oxy)phenyl)piperidine-1-carboxylate: To a suspension of NaH in DMF at 0° C. under inert atmosphere, a solution of tert-butyl 4-(3-hydroxyphenyl)piperidine-1-carboxylate (65 mg, 0.23 mmol) was added. The reaction mixture was warmed at rt and stirred for 30 min; then, dimethylcarbamic chloride (30 mg, 0.28 mmol) was added and the mixture was stirred at rt for 2 h. Ethyl acetate was added, washed with water, brine, dried over Na$_2$SO$_4$, filtered and concentrated under vacuum. Purification by flash chromatography, silica gel, gradient hexane to ethyl acetate afforded the title product (80 mg, 98% yield). $^1$H-NMR (400 MHz, CDCl$_3$), δ ppm: 7.29 (m, 1H), 7.04 (m, 1H), 4.24 (m, 2H), 3.11 (s, 3H), 3.03 (s, 3H), 2.79 (m, 2H), 2.66 (tt J=12, 3.5 Hz, 1H), 1.85 (m, 2H), 1.64 (m, 2H), 1.49 (s, 9H).

3-(Piperidin-4-yl)phenyl dimethylcarbamate: To a solution of 4-(3-((dimethylcarbamoyl)oxy)phenyl)piperidine-1-carboxylate (80 mg, 0.23 mmol) in dioxane (0.5 mL), a solution of 4M HCl in dioxane (0.86 mL, 3.44 mmol) was added, and the mixture was stirred at rt overnight. The solution was concentrated to dryness to afford the title compound (65 mg, 99% yield) as hydrochloride. $^1$H-NMR (500 MHz, MeOD) δ ppm: 7.37 (t, J=8 Hz, 1H), 7.17 (d, J=8 Hz, 1H), 7.04 (m, 1H), 7.00 (m, 1H), 3.51 (m, 2H), 3.15 (m, 2H), 3.14 (s, 3H), 3.01 (s, 3H), 2.95 (tt J=12, 3.5 Hz, 1H), 2.11 (m, 2H), 1.92 (m, 2H).

Example of Preparation of an Intermediate of Formula (V$_{ex}$), Method IIA

Synthesis of 3-(1-(prop-2-yn-1-yl)piperidin-4-yl)phenol

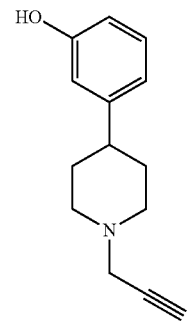

A suspension of 4-(3-hydroxyphenyl)piperidine (403 mg, 2.23 mmol), Et$_3$N (404 μl, 2.90 mmol) and propargyl bromide (273 μL, 80% wt in toluene, 2.45 mmol) in THF (20 mL) was irradiated with microwaves at 75° C. for 1 h. The reaction mixture was cooled and the solvent evaporated. Purification by flash chromatography, silica gel, gradient hexane to ethyl acetate afforded the desired product (352 mg, 73% yield). $^1$H-NMR (400 MHz, CDCl$_3$), δ ppm: 7.16 (t, J=8 Hz, 1H), 6.78 (d, J=8 Hz, 1H), 6.77 (m, 2H), 3.37 (d, J=2 Hz, 2H), 3.02 (d, J=11 Hz, 2H), 2.46 (m, 1H), 2.36 (td, J=11, 3 Hz, 2H), 2.28 (t, J=2 Hz, 1H), 1.84 (m, 4H).

Example of Preparation of an Intermediate of Formula (III$_{ex}$), Method VI

Synthesis of 1-(3-fluoropyridin-2-yl)methyl)-1H-1,2,3-triazole-4-carbaldehyde

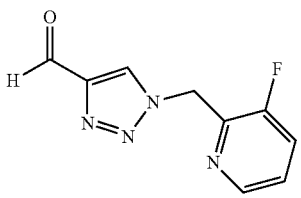 [SMILES: O=Cc1cn(Cc2ncccc2F)nn1]

To a solution of (1-((3-fluoropyridin-2-yl)methyl)-1H-1,2,3-triazol-4-yl)methanol (408 mg, 1.96 mmol) in dry dichloromethane (19 mL), MnO$_2$ (1.74 g, 17.6 mmol) was added and the mixture was stirred at rt overnight. The reaction mixture was filtered on Celite and the solvent was removed under vacuum. Purification by flash chromatography, silica gel, gradient hexane to ethyl acetate, afforded the title product (297 mg, 73% yield). $^1$H-NMR (400 MHz, CDCl$_3$), δ ppm: 10.16 (s, 1H), 8.43 (dt, J=4.7, 1.4 Hz, 1H), 8.36 (s, 1H), 7.51 (m, 1H), 7.39 (m, 1H), 5.83 (d, J=2 Hz, 2H).

Example of Preparation of an Intermediate of Formula (XIVa$_{ex}$), Method X

Synthesis of (1-((3-fluoropyridin-2-yl)methyl)-1H-1,2,3-triazol-4-yl)methanol

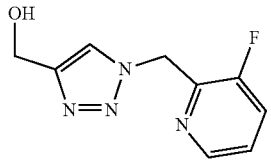 [SMILES: OCc1cn(Cc2ncccc2F)nn1]

To a solution of 2-(azidomethyl)-3-fluoropyridine (529 mg, 3.48 mmol), in MeOH (7.7 mL), propargyl alcohol (390 mg, 6.96 mmol) and a solution of Cu(OAc)$_2$ (44 mg, 0.24 mmol) in water (4 mL) were added and the mixture was stirred at rt overnight. The reaction mixture was filtered through alumina, washed with ethyl acetate and MeOH and the combined filtrates concentrated under vacuum. Purification was carried out by flash chromatography, silica gel, gradient dichloromethane to dichloromethane:methanol 8:2 to afford the title product (408 mg, 56% yield). $^1$H-NMR (400 MHz, CDCl$_3$), δ ppm: 8.41 (bs, 1H), 7.80 (bs, 1H), 7.44 (t, J=8 Hz, 1H), 7.34 (m, 1H), 5.72 (s, 2H), 4.77 (bs, 2H).

Example of Preparation of an Intermediate of Formula (Ice), Method IIB

Synthesis of 3-(1-((1-Pyridin-2-ylmethyl)-1H-1,2,3-triazol-4-yl)methyl)piperidin-4-yl)phenol

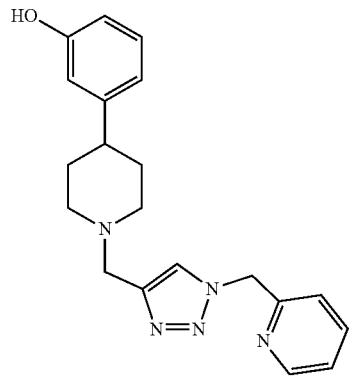 [SMILES: Oc1cccc(C2CCN(Cc3cn(Cc4ccccn4)nn3)CC2)c1]

A mixture of 3-(1-(prop-2-yn-1-yl)piperidin-4-yl)phenol (416 mg, 1.32 mmol), 2-(azidomethyl)pyridine (337 mg, 2.51 mmol), CuSO$_4$.5H$_2$O (48 mg, 0.19 mmol) and sodium ascorbate (77 mg, 0.38 mmol) in t-BuOH:H$_2$O 1:1 (32 mL) was stirred at rt for 16 h. Water and saturated NH$_4$Cl aqueous solution were added and the mixture extracted with EtOAc. The organic phases were combined, dried over Na$_2$SO$_4$ and concentrated. Purification was carried out by flash chromatography, silica gel, gradient hexane to acetone to afford the title product (525 mg, 78% yield). $^1$H-NMR (300 MHz, CDCl$_3$), δ ppm: 8.60 (m, 1H), 7.70 (td, J=7.6, 1.8 Hz, 1H), 7.68 (s, 1H), 7.28 (m, 1H), 7.20 (d, J=8 Hz, 1H), 7.13 (t, J=7.6 Hz, 1H), 6.74 (d, J=7.6 Hz, 1H), 6.66 (m, 2H), 5.65 (s, 2H), 3.73 (s, 2H), 3.06 (m, 2H), 2.44 (tt, J=11.4 Hz, 1H), 2.17 (m, 2H), 1.78 (m, 4H).

SYNTHESIS OF EXAMPLES

Preparation of Compounds of General Formula (I$_{ex}$), Method I

Example 1

3-(1-((1-phenyl-1H-1,2,3-triazol-4-yl)methyl)piperidin-4-yl)phenyl ethylcarbamate

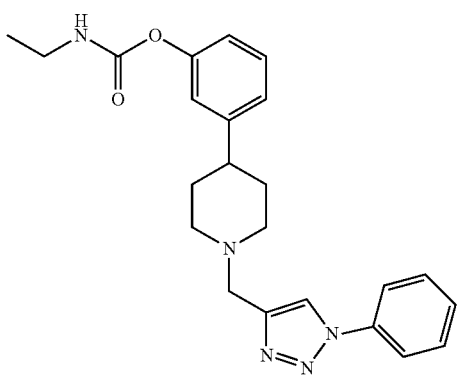 [SMILES: CCNC(=O)Oc1cccc(C2CCN(Cc3cn(-c4ccccc4)nn3)CC2)c1]

To a suspension of 3-(piperidin-4-yl)phenyl dimethylcarbamate hydrochloride (38 mg, 0.13 mmol) in dichloroethane (3 mL), DIPEA (163 μL, 0.93 mmol) was added and the mixture was stirred at rt for 5 min. Then, 1-phenyl-1H-1,2,3-triazole-4-carbaldehyde (30 mg, 0.17 mmol) and NaBH(OAc)$_3$ (45 mg, 0.21 mmol) were added and the reaction mixture was stirred at rt overnight. Dichloromethane was added and washed with NaHCO$_3$ sat solution and brine, dried over Na$_2$SO$_4$, filtered and concentrated. Purification by flash chromatography, silica gel, gradient dichloromethane to dichloromethane: methanol 90:10 afforded the title product (40 mg, 73% yield). HPLC retention time: 5.62 min; HRMS: 406.2227 (M+H).

This method was used for the preparation of examples 1, 8, 10, 11, 12, 15, 16, 17.

Preparation of Compounds of General Formula (I$_{ex}$), Method IIF

Example 2

1-((1-4-fluorophenyl)-1H-1,2,3-triazol-4-yl)methyl) 4-(3-methoxy-phenyl)piperidine

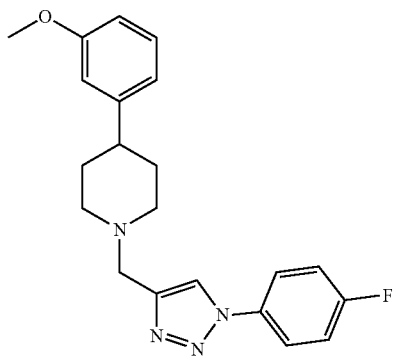 [SMILES: COc1cccc(C2CCN(Cc3cn(-c4ccc(F)cc4)nn3)CC2)c1]

A mixture of 4-(3-methoxyphenyl)piperidine (61 mg, 0.32 mmol), Et$_3$N (178 μl, 1.27 mmol) and propargyl bromide (36 μL, 0.32 mmol, 80% solution in toluene) in water (1.2 mL) was vigorously stirred at rt for 1 h. Then, 4-fluorophenylazide (670 μL, 0.5M solution in tert-butylmethylether, 0.33 mmol) and CuI (6 mg, 0.03 mmol) were added. The mixture was stirred at rt overnight. NH$_4$Cl saturated solution was added and the mixture was extracted with EtOAc, washed with brine, dried over Na$_2$SO$_4$, filtered and concentrated. Purification by flash chromatography, silica gel, gradient from hexane to hexane:ethyl acetate (1:1) afforded the titled product (70 mg, 60% yield). HPLC retention time: 5.91 min; HRMS: 367.1946 (M+H).

This method was used for the preparation of the examples of formula (I) 2, 7.

Preparation of Compounds of General Formula (Id$_{ex}$), Method III

Example 3

3-(1-((1-(pyridine-2-ylmethyl)-1H-1,2,3-triazol-4-yl) methyl)piperidin-4-yl)phenyl acetate

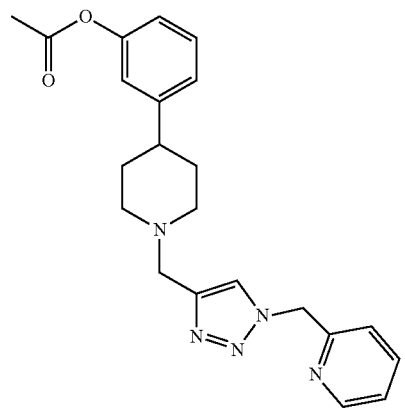 [SMILES: CC(=O)Oc1cccc(C2CCN(Cc3cn(Cc4ccccn4)nn3)CC2)c1]

To a solution of 3-(1-((1-pyridin-2-ylmethyl)-1H-1,2,3-triazol-4-yl)methyl)piperidin-4-yl)phenol (130 mg, 0.37 mmol) in DCM (6 mL), Et$_3$N (156 μL, 1.12 mmol) and 4-DMAP (9 mg, 0.07 mmol) were added. The reaction mixture was cooled at 0° C. and acetic anhydride (42 mL, 0.44 mmol) was added. The reaction mixture was warmed at rt and stirred overnight, NaHCO$_3$ saturated solution was added and extracted with DCM, washed with brine, dried over Na$_2$SO$_4$, filtered and concentrated. Purification by flash chromatography silica gel, gradient from DCM to DCM:MeOH (95:5) afforded the title product (130 mg, 89% yield). HPLC retention time: 4.97 min; HRMS: 392.2079 (M+H).

This method was used for the preparation of examples of formula (I) 3, 9.

Preparation of Compounds of General Formula (Ie$_{ex}$), Method III

Example 4

4-(((3-(1-((1-(pyridin-2-yl methyl)-1H-1,2,3-triazol-4-yl)methyl)piperidin-4-yl)phenoxy)carbonyl) amino)benzoic acid

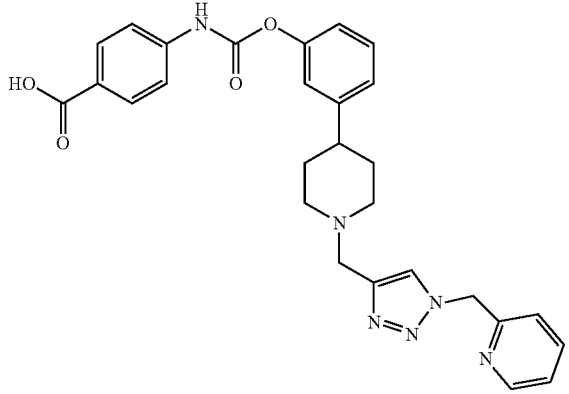 [SMILES: O=C(Nc1ccc(C(=O)O)cc1)Oc1cccc(C2CCN(Cc3cn(Cc4ccccn4)nn3)CC2)c1]

tert-Butyl 4-(((3-(1-((1-(pyridin-2-ylmethyl)-1H-1,2,3-triazol-4-yl)methyl)piperidin-4-yl)phenoxy)carbonyl) amino)benzoate: A mixture of 3-(1-((1-pyridin-2-ylmethyl)-

1H-1,2,3-triazol-4-yl)methyl)piperidin-4-yl)phenol (340 mg, 0.397 mmol) and tert-butyl-4-isocyanatobenzoate (300 mg, 1.36 mmol) in THF (10 mL) under inert atmosphere, was heated at 70° C. in a sealed tube for 16 h. The reaction mixture was cooled down to rt and concentrated under vacuum. Purification by flash chromatography silica gel, gradient from DCM to DCM:MeOH (90:10) afforded the title product (350 mg, 63% yield). $^1$H-NMR (400 MHz, MeOD), δ ppm: 8.62 (m, 1H), 8.11 (s, 1H), 7.98 (d AB system, 2H), 7.92 (td, J=7.5, 1.8 Hz, 1H), 7.65 (d AB system, 2H), 7.45 (m, 1H), 7.40 (t, J=8 Hz, 2H), 7.21 (d, J=8 Hz, 1H), 7.15 (t, J=2 Hz, 1H), 7.10 (m, 1H), 5.80 (s, 2H), 3.82 (s, 2H), 3.15 (m, 2H), 2.65 (tt, J=12, 4 Hz, 1H), 2.33 (m, 2H), 1.89 (m, 4H), 1.66 (s, 9H).

4-(((3-(1-((1-(Pyridin-2-ylmethyl)-1H-1,2,3-triazol-4-yl)methyl)piperidin-4-yl)phenoxy)carbonyl)amino)benzoic acid: To a suspension of tert-butyl 4-(((3-(1-((1-(pyridin-2-ylmethyl)-1H-1,2,3-triazol-4-yl)methyl)piperidin-4-yl)phenoxy)carbonyl)amino)benzoate (175 mg, 0.31 mmol) in dioxane (1 mL), a solution of 4M HCl in dioxane (1 mL, 4 mmol) was added and the mixture was stirred at rt for 6 h. The solid was isolated by filtration to afford the titled product (151 mg, 79% yield) as hydrochloride. HPLC retention time: 5.13 min; HRMS: 511.2104 (M−H).

This method was used for the preparation of examples of formula (I) 4, 13, 14.

Preparation of Compounds of General Formula (Iq$_{ex}$), Method III

Example 5

3-(1-((1-(pyridin-2-ylmethyl)-1H-1,2,3-triazol-4-yl)methyl)piperidin-4-yl)phenyl isobutyrate

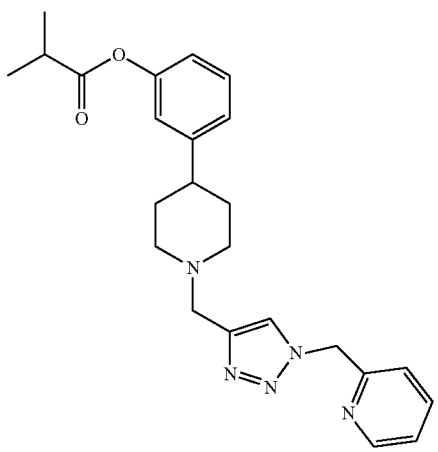 [SMILES: CC(C)C(=O)Oc1cccc(C2CCN(Cc3cn(Cc4ccccn4)nn3)CC2)c1]

To a solution of 3-(1-((1-pyridin-2-ylmethyl)-1H-1,2,3-triazol-4-yl)methyl)piperidin-4-yl)phenol (200 mg, 0.57 mmol) in anhydrous THF (10 mL) at 0° C., Et$_3$N (160 µl, 1.15 mmol) and isobutyryl chloride (91 mg, 0.86 mmol) were added. The reaction mixture was stirred at 0° C. for 10 min and then at rt for 4 h. The reaction mixture was cooled again at 0° C. and additional amount of isobutyryl chloride (45 mg, 0.43 mmol) was added and stirred at rt for 2 h until completed reaction. NaHCO$_3$ saturated solution was added and extracted with DCM, washed with brine, dried over Na$_2$SO$_4$, filtered and concentrated to afforded the title product (209 mg, 87% yield). HPLC retention time: 5.67 min; HRMS: 420.2395 (M+H).

This method was used for the preparation of examples of formula (I) 5.

Preparation of Compounds of General Formula (Iq$_{ex}$), Method III

Example 6

(S)-3-(1-((1-pyridin-2-ylmethyl)-1H-1,2,3-triazol-4-yl)methyl)piperidin-4-yl)phenyl 2-amino-3-methyl butanoate

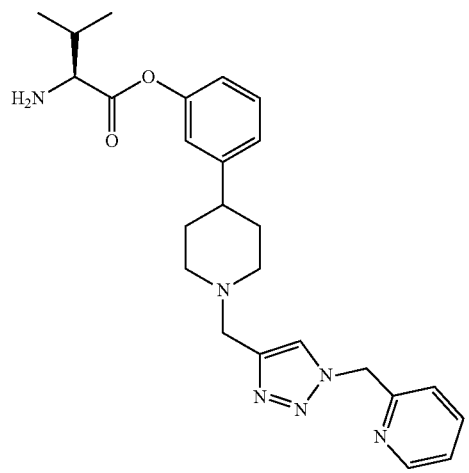 [SMILES: CC(C)[C@H](N)C(=O)Oc1cccc(C2CCN(Cc3cn(Cc4ccccn4)nn3)CC2)c1]

(S)-3-(1-((1-Pyridin-2-ylmethyl)-1H-1,2,3-triazol-4-yl)methyl)piperidin-4-yl)phenyl 2-((tert-butoxycarbonyl)amino-3-methylbutanoate: To a solution of 3-(1-((1-pyridin-2-ylmethyl)-1H-1,2,3-triazol-4-yl)methyl)piperidin-4-yl)phenol (300 mg, 0.86 mmol) and Boc-(L)-Val-OH (261 mg, 1.20 mmol) in anhydrous DCM (20 mL) under inert atmosphere, EDAC-HCl (247 mg, 1.28 mmol) and 4-DMAP (52 mg, 0.43 mmol) were added. The reaction mixture was stirred at rt for 16 h. DCM was added and washed with water and brine, dried over Na$_2$SO$_4$, filtered and concentrated. Purification by flash chromatography, silica gel, gradient from DCM to DCM:MeOH (90:10) afforded the title product (440 mg, 93% yield). $^1$H-NMR (400 MHz, MeOD), δ ppm: 8.61 (m, 1H), 7.69 (td, J=7.5, 1.8 Hz, 1H), 7.67 (s, 1H), 7.29 (m, 2H), 7.20 (d, J=8 Hz, 1H), 7.09 (d, J=8 Hz, 1H), 6.92 (m, 2H), 5.66 (s, 2H), 5.10 (d, J=9 Hz, 1H), 4.45 (m, 1H), 3.72 (s, 2H), 3.07 (m, 2H), 2.50 (tt, J=12, 4 Hz, 1H), 2.32 (m, 1H), 2.17 (td, J=12, 2 Hz, 2H), 1.79 (m, 4H), 1.47 (s, 9H), 1.08 (d, J 6.8 Hz, 3H), 1.02 (d, J 6.8 Hz, 3H).

(S)-3-(1-((1-Pyridin-2-ylmethyl)-1H-1,2,3-triazol-4-yl)methyl)piperidin-4-yl)phenyl 2-amino-3-methylbutanoate: To a solution of (S)-3-(1-((1-pyridin-2-ylmethyl)-1H-1,2,3-triazol-4-yl)methyl)piperidin-4-yl)phenyl 2-((tert-butoxycarbonyl)amino-3-methylbutanoate (540 mg, 0.98 mmol) in dioxane (3 mL), ), a solution of 4M HCl in dioxane (3.7 mL, 14.7 mmol) was added and the mixture was stirred at rt for 2 h. The reaction mixture was concentrated to dryness to afford the title product (455 mg, 89% yield) as hydrochloride. HPLC retention time: 4.28 min; MS: 471.3 (M+Na).

This method was used for the preparation of examples of formula (I) 6, 18, 19, 20.

Table of Examples with Results of HRMS and Binding to the μ-opioid Receptor and the σ1-Receptor:

HPLC:
 column: Agilent Eclipse XDB-C18, 4.6×150 mm, 5 mm, flux: 1 ml/min. A:H₂O (0.05% TFA), B:ACN.

Conditions: 1°/gradient 5% to 95% B in 7 min. 2°/isocratic 95% B 5 min.

HRMS:
 Source type: ESI; Ion Polarity: Positive or Negative

| EX | Structure | Chemical name | Ret time (min) | HRMS |
|---|---|---|---|---|
| 1 | 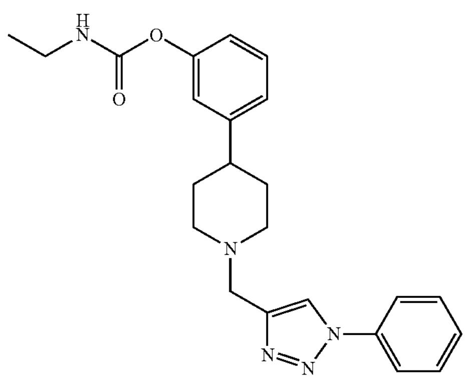 [SMILES: CCNC(=O)Oc1cccc(C2CCN(Cc3cn(-c4ccccc4)nn3)CC2)c1] | 3-(1-((1-phenyl-1H-1,2,3-triazol-4-yl)methyl)piperidin-4-yl)phenyl ethylcarbamate | 5.62 | 406.2227 (M + H) |
| 2 | 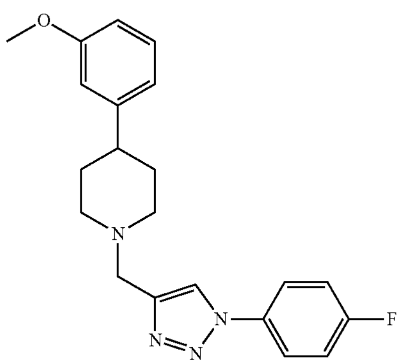 [SMILES: COc1cccc(C2CCN(Cc3cn(-c4ccc(F)cc4)nn3)CC2)c1] | 1-((1-(4-fluorophenyl)-1H-1,2,3-triazol-4-yl)methyl)-4-(3-methoxyphenyl)piperidine | 5.91 | 367.1946 (M + H) |
| 3 | 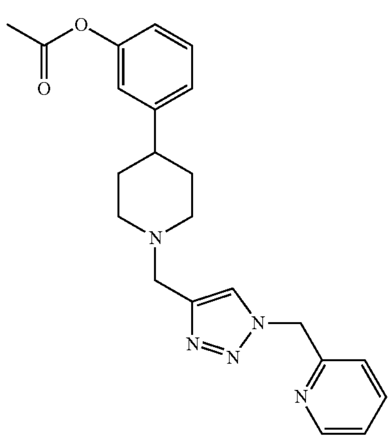 [SMILES: CC(=O)Oc1cccc(C2CCN(Cc3cn(Cc4ccccn4)nn3)CC2)c1] | 3-(1-((1-(pyridin-2-ylmethyl)-1H-1,2,3-triazol-4-yl)methyl)piperidin-4-yl)phenyl acetate | 4.97 | 392.2079 (M + H) |

-continued

| EX | Structure | Chemical name | Ret time (min) | HRMS |
|---|---|---|---|---|
| 4 | 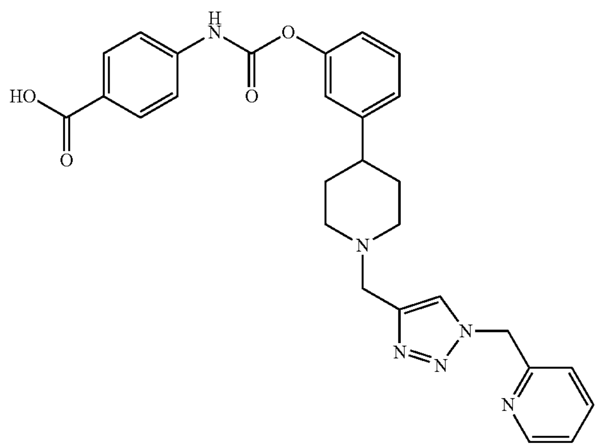 [SMILES: O=C(Nc1ccc(C(=O)O)cc1)Oc1cccc(C2CCN(Cc3cn(Cc4ccccn4)nn3)CC2)c1] | 4-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonyl amino)benzoic acid | 5.13 | 511.2104 (M − H) |
| 5 | 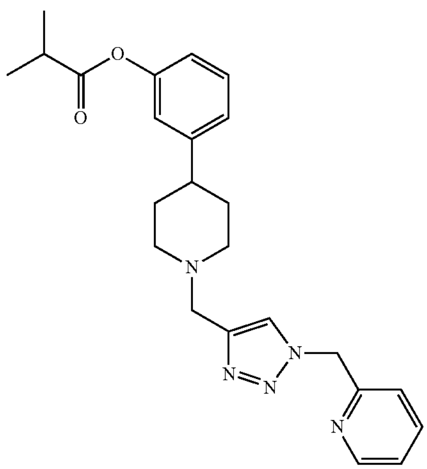 [SMILES: CC(C)C(=O)Oc1cccc(C2CCN(Cc3cn(Cc4ccccn4)nn3)CC2)c1] | 3-(1-((1-(pyridin-2-ylmethyl)-1H-1,2,3-triazol-4-yl)methyl)piperidin-4-yl)phenyl isobutyrate | 5.67 | 420.2395 (M + H) |
| 6 | 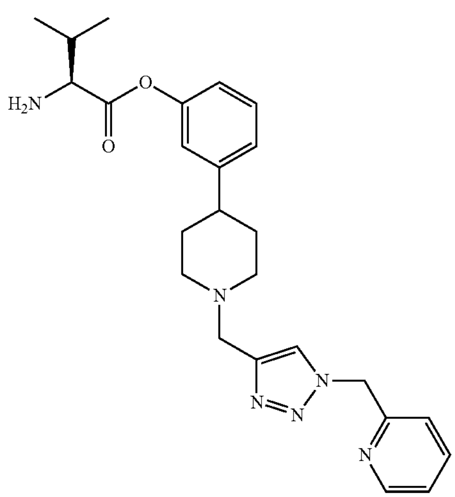 [SMILES: CC(C)[C@H](N)C(=O)Oc1cccc(C2CCN(Cc3cn(Cc4ccccn4)nn3)CC2)c1] | (S)-3-(1-((1-(pyridin-2-ylmethyl)-1H-1,2,3-triazol-4-yl)methyl)piperidin-4-yl)phenyl 2-amino-3-methylbutanoate | 4.28 | 471.3 (M + Na) |

-continued

| EX | Structure | Chemical name | Ret time (min) | HRMS |
|---|---|---|---|---|
| 7 | 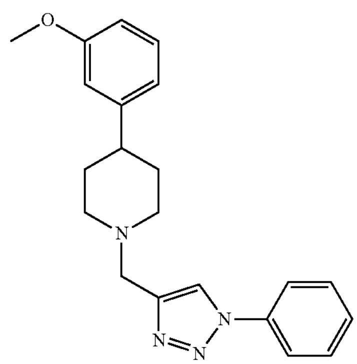 [SMILES: COc1cccc(C2CCN(Cc3cn(-c4ccccc4)nn3)CC2)c1] | 4-(3-methoxyphenyl)-1-((1-phenyl-1H-1,2,3-triazol-4-yl)methyl)piperidine | 5.84 | 349.2036 (M + H) |
| 8 | 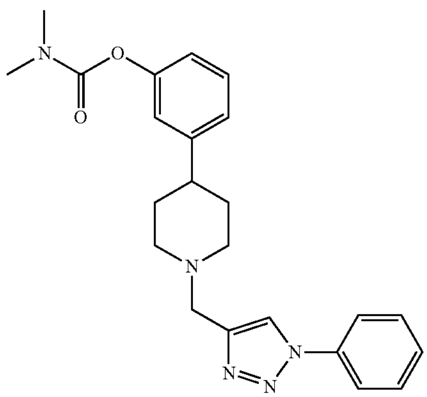 [SMILES: CN(C)C(=O)Oc1cccc(C2CCN(Cc3cn(-c4ccccc4)nn3)CC2)c1] | 3-(1-((1-phenyl-1H-1,2,3-triazol-4-yl)methyl)piperidin-4-yl)phenyl dimethylcarbamate | 5.65 | 406.2255 (M + H) |
| 9 | 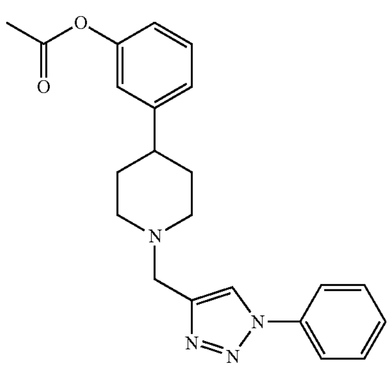 [SMILES: CC(=O)Oc1cccc(C2CCN(Cc3cn(-c4ccccc4)nn3)CC2)c1] | 3-(1-((1-phenyl-1H-1,2,3-triazol-4-yl)methyl)piperidin-4-yl)phenyl acetate | 5.70 | 377.1974 (M + H) |
| 10 | 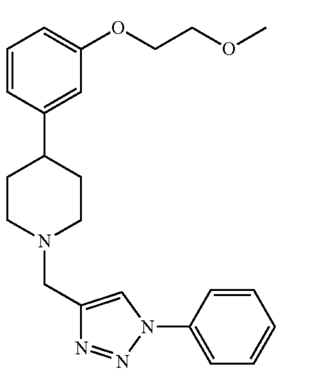 [SMILES: COCCOc1cccc(C2CCN(Cc3cn(-c4ccccc4)nn3)CC2)c1] | 4-(3-(2-methoxyethoxy)phenyl)-1-((1-phenyl-1H-1,2,3-triazol-4-yl)methyl)piperidine | 5.75 | 393.2309 (M + H) |

| EX | Structure | Chemical name | Ret time (min) | HRMS |
|---|---|---|---|---|
| 11 | 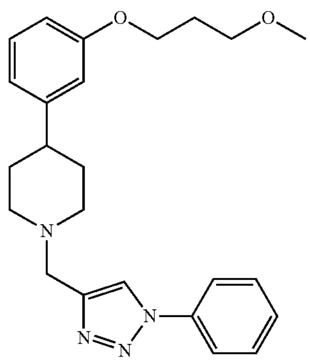 [SMILES: COCCCOc1cccc(C2CCN(Cc3cn(-c4ccccc4)nn3)CC2)c1] | 4-(3-(3-methoxypropoxy)phenyl)-1-((1-phenyl-1H-1,2,3-triazol-4-yl)methyl)piperidine | 5.87 | 407.2457 (M + H) |
| 12 | 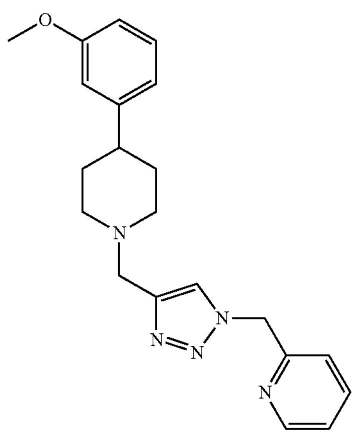 [SMILES: COc1cccc(C2CCN(Cc3cn(Cc4ccccn4)nn3)CC2)c1] | 2-((4-((4-(3-methoxyphenyl)piperidin-1-yl)methyl)-1H-1,2,3-triazol-1-yl)methyl)pyridine | 5.06 | 364.2128 (M + H) |
| 13 | 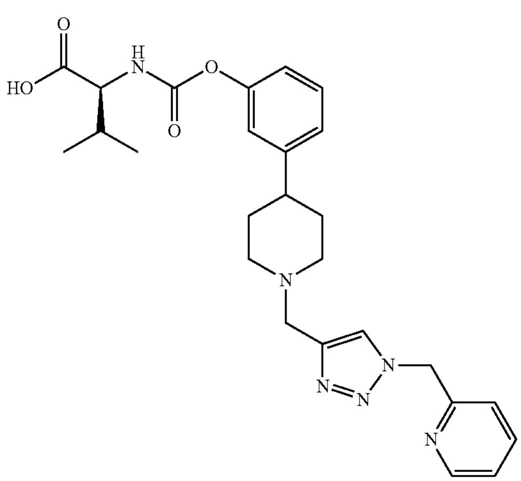 [SMILES: CC(C)[C@H](NC(=O)Oc1cccc(C2CCN(Cc3cn(Cc4ccccn4)nn3)CC2)c1)C(=O)O] | (S)-3-methyl-2-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonyl amino)butanoic acid | 5.05 | 491.2424 (M − H) |

-continued

| EX | Structure | Chemical name | Ret time (min) | HRMS |
|----|-----------|---------------|----------------|------|
| 14 | 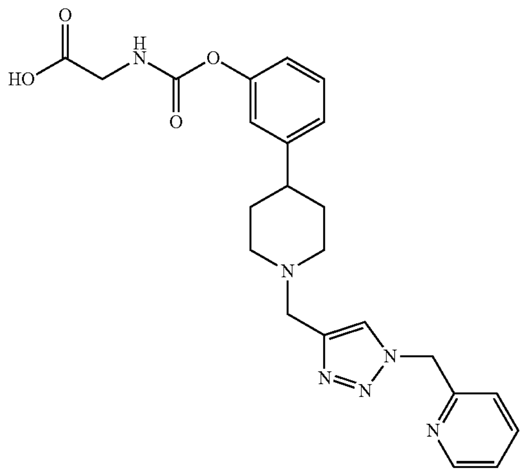 [SMILES: O=C(O)CNC(=O)Oc1cccc(C2CCN(Cc3cn(Cc4ccccn4)nn3)CC2)c1] | 2-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonyl amino)acetic acid | 4.45 | 449.1944 (M − H) |
| 15 | 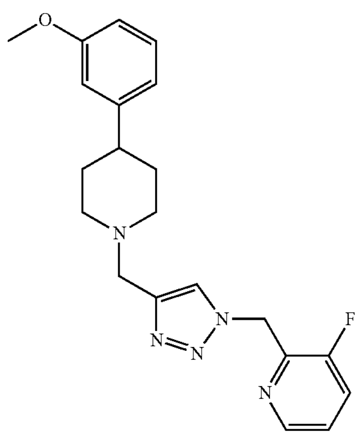 [SMILES: COc1cccc(C2CCN(Cc3cn(Cc4ncccc4F)nn3)CC2)c1] | 3-fluoro-2-((4-((4-(3-methoxyphenyl)piperidin-1-yl)methyl)-1H-1,2,3-triazol-1-yl)methyl)pyridine | 5.33 | 382.2041 (M + H) |
| 16 | 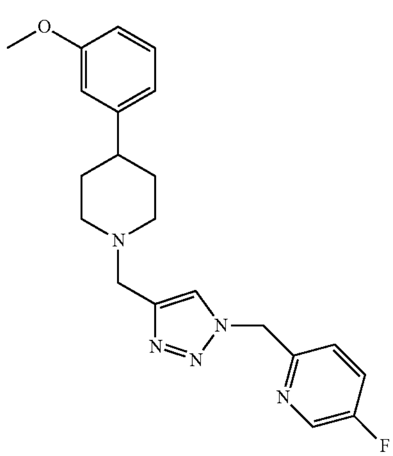 [SMILES: COc1cccc(C2CCN(Cc3cn(Cc4ccc(F)cn4)nn3)CC2)c1] | 5-fluoro-2-((4-((4-(3-methoxyphenyl)piperidin-1-yl)methyl)-1H-1,2,3-triazol-1-yl)methyl)pyridine | 5.36 | 382.2040 (M + H) |

| EX | Structure | Chemical name | Ret time (min) | HRMS |
|---|---|---|---|---|
| 17 | 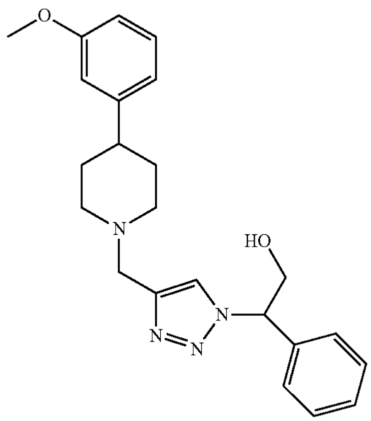 [SMILES: COc1cccc(C2CCN(Cc3cn(C(CO)c4ccccc4)nn3)CC2)c1] | 2-(4-((4-(3-methoxyphenyl)piperidin-1-yl)methyl)-1H-1,2,3-triazol-1-yl)-2-phenylethanol | 5.58 | 393.2292 (M + H) |
| 18 | 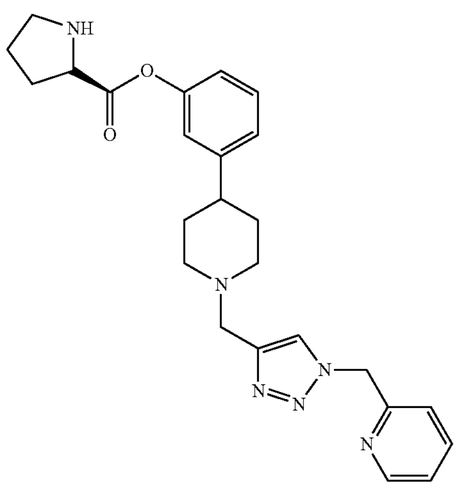 | (S)-3-(1-((1-(pyridin-2-ylmethyl)-1H-1,2,3-triazol-4-yl)methyl)piperidin-4-yl)phenyl pyrrolidine-2-carboxylate | 4.12 | 469.3 (M + Na) |
| 19 | 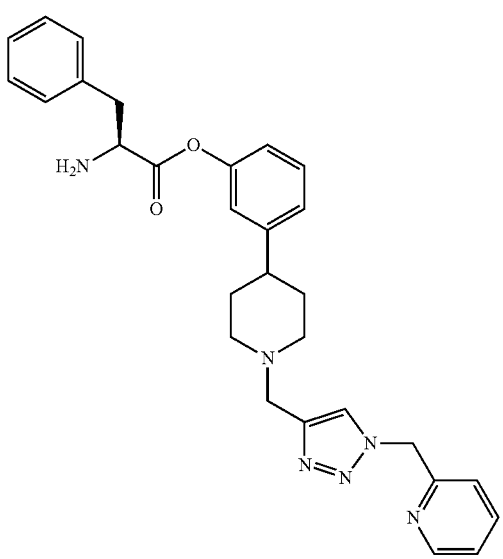 [SMILES: N[C@@H](Cc1ccccc1)C(=O)Oc1cccc(C2CCN(Cc3cn(Cc4ccccn4)nn3)CC2)c1] | (S)-3-(1-((1-(pyridin-2-ylmethyl)-1H-1,2,3-triazol-4-yl)methyl)piperidin-4-yl)phenyl 2-amino-3-phenylpropanoate | 4.70 | 519.3 (M + Na) |

| EX | Structure | Chemical name | Ret time (min) | HRMS |
|---|---|---|---|---|
| 20 | 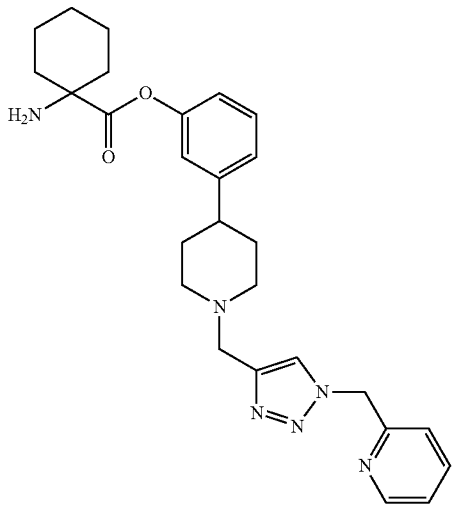 [SMILES: NC1(C(=O)Oc2cccc(C3CCN(Cc4cn(Cc5ccccn5)nn4)CC3)c2)CCCCC1] | 3-(1-((1-(pyridin-2-ylmethyl)-1H-1,2,3-triazol-4-yl)methyl)piperidin-4-yl)phenyl 1-aminocyclohexane-carboxylate | | |

Biological Activity
Pharmacological Study
Human $\sigma_1$ Receptor Radioligand Assay To investigate binding properties of $\sigma_1$ receptor ligands to human $\sigma_1$ receptor, transfected HEK-293 membranes and [$^3$H](+)-pentazocine (Perkin Elmer, NET-1056), as the radioligand, were used. The assay was carried out with 7 µg of membrane suspension, 5 nM of [$^3$H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-Opioid Receptor Radioligand Assay To investigate binding properties of µ-opioid receptor ligands to human µ-opioid receptor, transfected CHO-K1 cell membranes and [$^3$H]-DAMGO (Perkin Elmer, ES-542-C), as the radioligand, were used. The assay was carried out with 20 µg of membrane suspension, 1 nM of [$^3$H]-DAMGO in either absence or presence of either buffer or 10 µM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the µ-opiod receptor it is a very preferred embodiment in which the compounds are selected which act as dual ligands of the $\sigma_1$ receptor and the µ-opiod receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the µ-opiod receptor expressed as $K_i$:

+ Both $K_i$-µ and $K_i$-$\sigma_1$ >=500 nM

++ One $K_i$<500 nM while the other $K_i$ is >=500 nM

+++ Both $K_i$-µ and $K_i$-$\sigma_1$<500 nM

++++ Both $K_i$-µ and $K_i$-$\sigma_1$<100 nM

All compounds prepared in the present application exhibit binding to the $\sigma_1$ receptor and the µ-opiod receptor, in particular the following binding results are shown:

| EX | µ and $\sigma_1$ dual binding |
|---|---|
| 1 | +++ |
| 2 | ++ |
| 3 | ++ |
| 4 | +++ |
| 5 | +++ |
| 6 | +++ |
| 7 | +++ |
| 8 | +++ |
| 9 | ++++ |
| 10 | +++ |
| 11 | +++ |
| 12 | ++ |
| 13 | + |
| 14 | + |
| 15 | ++ |
| 16 | ++ |
| 17 | ++ |
| 18 | +++ |
| 19 | +++ |
| 20 | + |

The invention claimed is:
1. A compound of formula V:

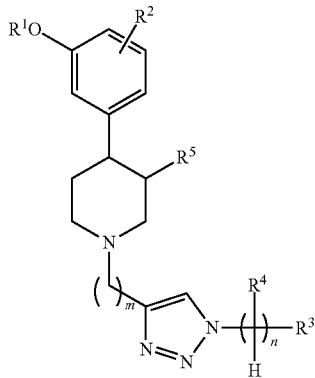

wherein
m is 1 or 2;
n is 0 or 1;
$R^1$ is —$COR^6$, —$CONR^8R^9$, —$COCR^6R^7NR^8R^9$, or substituted or unsubstituted $C_{1-4}$alkyl;
$R^2$ is hydrogen, halogen, or substituted or unsubstituted $C_{1-4}$alkyl;
$R^3$ is substituted or unsubstituted aryl or substituted or unsubstituted heterocyclyl;
$R^4$ is hydrogen, substituted or unsubstituted $C_{1-4}$alkyl;
$R^5$ is hydrogen, halogen or hydroxyl;
$R^6$, $R^7$, $R^8$ and $R^9$ are independent from each other and selected from the group consisting of hydrogen, substituted or unsubstituted $C_{1-4}$alkyl, substituted or unsubstituted phenyl, substituted or unsubstituted heterocyclyl or substituted or unsubstituted benzyl, or $R^6$ and $R^7$ together with their connecting atom form an unsubstituted 5- or 6-membered saturated cycloalkylic ring;
optionally as a stereoisomer, including enantiomers and diastereomers, a racemate or a mixture of at least two stereoisomers, including enantiomers and/or diastereomers, in any mixing ratio, or a salt thereof, or a solvate thereof.

2. The compound according to claim 1, wherein
m is 1;
$R^1$ is —$COR^6$, —$CONR^8R^9$, —$COR^6R^7NR^8R^9$, —$CH_3$, —$C_2H_4OCH_3$, or —$C_3H_6OCH_3$;
$R^2$ is hydrogen;
$R^3$ is substituted or unsubstituted phenyl or substituted or unsubstituted pyridine;
$R^4$ is hydrogen or —$CH_2OH$;
$R^5$ is hydrogen;
$R^6$, $R^7$, $R^8$ and $R^9$ are independent from each other selected from the group consisting of hydrogen, —$CH_3$, —CHCOOH, —$C_2H_5$, —$C_3H_7$, —CH($NH_2$)$C_3H_7$, —CH(COOH)$C_3H_7$, substituted phenyl, unsubstituted pyrrolidine, unsubstituted benzyl, or $R^6$ and $R^7$ together with their connecting carbon atom form an unsubstituted cyclohexyl ring.

3. The compound according claim 1, which is selected from:
3-(1-((1-phenyl-1H-1,2,3-triazol-4-yl)methyl)piperidin-4-yl)phenyl ethylcarbamate,
1-((1-(4-fluorophenyl)-1H-1,2,3-triazol-4-yl)methyl)-4-(3-methoxyphenyl)piperidine,
3-(1-((1-(pyridin-2-ylmethyl)-1H-1,2,3-triazol-4-yl)methyl)piperidin-4-yl)phenyl acetate,
4-((3-(1-((1-(pyridin-2-ylmethyl-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)benzoic acid,
3-(1-((1-(pyridin-2-ylmethyl)-1H-1,2,3-triazol-4-yl)methyl)piperidin-4-yl)phenyl isobutyrate,
(S)-3-(1-((1-(pyridin-2-ylmethyl)-1H-1,2,3-triazol-4-yl)methyl)piperidin-4-yl)phenyl 2-amino-3-methylbutanoate,
4-(3-methoxyphenyl)-1-((1-phenyl-1H-1,2,3-triazol-4-yl)methyl)piperidine,
3-(1-((1-phenyl-1H-1,2,3-triazol-4-yl)methyl)piperidin-4-yl)phenyl dimethylcarbamate,
3-(1-((1-phenyl-1H-1,2,3-triazol-4-yl)methyl)piperidin-4-yl)phenyl acetate,
4-(3-(2-methoxyethoxy)phenyl)-1-((1-phenyl-1H-1,2,3-triazol-4-yl)methyl)piperidine,
4-(3-(3-methoxypropoxy)phenyl)-1-((1-phenyl-1H-1,2,3-triazol-4-yl)methyl)piperidine,
2-((4-((4-(3-methoxyphenyl)piperidin-1-yl)methyl)-1H-1,2,3-triazol-1-yl)methyl)pyridine,
(S)-3-methyl-2-((3-(1-((1-(pyridin-2-ylmethyl)-1H-1,2,3-triazol-4-yl)methyl)piperidin-4-yl)phenylpyridin-2-ylmethyl)-1H-1,2,3-triazol-4-yl)methyl)piperidin-4-yl)phenoxy)carbonylamino)butanoic acid,
2-((3-(1-((1-(pyridin-2-ylmethyl-1H-1,2,3-triazol-yl)methyl)piperidin-4-yl)phenylpyridin-2-ylmethyl)-1H-1,2,3-triazol-4-yl)methyl)piperidin-4-yl)phenoxy)carbonylamino)acetic acid,
3-fluoro-2-((4-((4-(3-methoxyphenyl)piperidin-1-yl)methyl)-1H-1,2,3-triazol-1-yl)methyl)pyridine,
5-fluoro-2-((4-((4-(3-methoxyphenyl)piperidin-1-yl)methyl)-1H-1,2,3-triazol-1-yl)methyl)pyridine,
2-(4-((4-(3-methoxyphenyl)piperidin-1-yl)methyl)-1H-1,2,3-triazol-1-yl)-2-phenylethanol,
(S)-3-(1-((1-(pyridin-2-ylmethyl)-1H-1,2,3-triazol-4-yl)methyl)piperidin-4-yl)phenyl pyrrolidine-2-carboxylate,
(S)-3-(1-((1-(pyridin-2-ylmethyl)-1H-1,2,3-triazol-4-yl)methyl)piperidin-4-yl)phenyl 2-amino-3-phenylpropanoate, and
3-(1-((1-(pyridin-2-ylmethyl)-1H-1,2,3-triazol-4-yl)methyl)piperidin-4-yl)phenyl 1-aminocyclohexanecarboxylate
optionally as a stereoisomer, including enantiomers and diastereomers, a racemate or in form of a mixture of at least two stereoisomers, including enantiomers and/or diastereomers, in any mixing ratio, or a salt thereof, or a solvate thereof.

4. The compound according claim 3, which is selected from:
3-(1-((1-phenyl-1H-1,2,3-triazol-4-yl)-methyl)piperidin-4-yl)phenyl ethylcarbamate,
3-(1-((1-pyridin-2-ylmethyl)-1H-1,2,3-triazol-4-yl)methyl)piperidin-4-yl)phenyl acetate,
4-((3-(1-((1-(pyridin-2-ylmethyl)-1H-1,2,3-triazol-4-yl)methyl)piperidin-4-yl)phenylpyiridin-2-ylmethyl)-1H-1,2,3-triazol-yl)methyl)piperidin-4-yl)phenoxy)carbonylamino)benzoic acid,
3-(1-((1-(pyridin-2-ylmethyl)-1H-1,2,3-triazol-4-yl)methyl)piperidin-4-yl)phenyl isobutyrate,
(S)-3-(1-((1-(pyridin-2-ylmethyl)-1H-1,2,3-triazol-4-yl)methyl)piperidin-4-yl)phenyl 2-amino-3-methylbutanoate, 4-(3-methoxyphenyl)-1-((1-phenyl-1H-1,2,3-triazol-4-yl)methyl)piperidine, 3-(1-((1-phenyl-1H-1,2,3-triazol-4-yl)methyl)piperidin-4-yl)phenyl dimethylcarbamate, 3-(1-((1-phenyl-1H-1,2,3-triazol-4-yl)methyl)piperidin-4-yl)phenyl acetate, 4-(3-(2-methoxyethoxy)phenyl)-1-((1-phenyl-1H-1,2,3-triazol-4-yl)methyl)piperidine, 4-(3-(3-methoxypropoxy)phenyl)-1-((1-phenyl-1H-1,2,3-triazol-4-yl)methyl)piperadine, (S)-3-(1-((1-(pyridin-2-ylmethyl)-1H-1,2,3-triazol-4-yl)methyl)piperidin-4-yl)phenyl pyrrolidine-2-carboxylate, (S)-3-(1-((1-(pyridin-2-ylmethyl)-1H-1,2,3-triazol-4-yl)methyl)piperidin-4-yl)phenyl 2-amino-3-phenylpropanoate, and 3-(1-((1-(pyridin-2-ylmethyl)-1H-1,2,3-triazol-4-yl)methyl)piperidin-4-yl)phenyl 1-aminocyclohexanecarboxylate;

optionally as a stereoisomer, including enantiomers and diastereomers, a racemate or in form of a mixture of at least two stereoisomers, including enantiomers and/or diastereomers, in any mixing ratio, or a salt thereof, or a solvate thereof.

5. The compound according claim 4, which is selected from:

3-(1-((1-phenyl-1H-1,2,3-triazol-yl)methyl)piperidin-4-yl)phenyl acetate, and 3-(1-((1-(pyridin-2-ylmethyl)-1H-1,2,3-triazol-4-yl)methyl)piperidin-4-yl)phenyl acetate;

optionally as a stereoisomer, including enantiomers and diastereomers, a racemate or in form of a mixture of at least two stereoisomers, including enantiomers and/or diastereomers, in any mixing ratio, or a salt thereof, or a solvate thereof.

6. A process for the production of a compound of formula V according to claim 1:

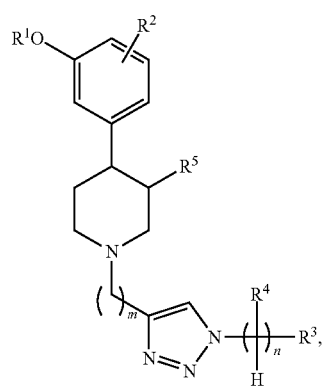

(V)

wherein $R^1$, $R^2$, $R^3$, $R^4$, $R^5$, n and m are as defined in claim 1, wherein a compound of formula VI or a salt thereof, including a hydrochloride salt,

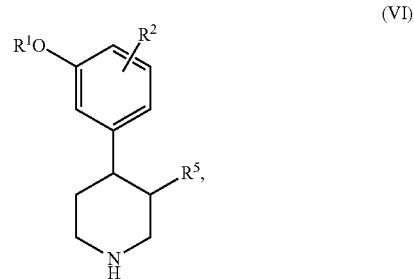

(VI)

wherein $R^1$, $R^2$, and $R^5$ are as defined in claim 1, is reacted with a compound according to formula VIII under the conditions of Step 2

(VIII)

wherein m is as defined in claim 1, leading to a compound according to formula VII,

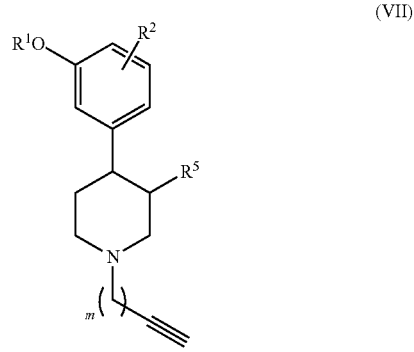

(VII)

wherein $R^1$, $R^2$, $R^5$ and m are as defined in claim 1, followed by reacting said compound according to formula VII with a compound according to formula IX under the conditions of Step 3

(IX)

wherein $R^3$, $R^4$ and n are as defined in claim 1, under the conditions of Step 3, leading to a compound according to formula (V), wherein X is a leaving group, including a halogen or sulphate, wherein the reaction of Step 2 of said compounds of general formula (VI) with said compounds of formula (VIII) is carried out in the presence of a base in an aprotic solvent;

wherein the reaction of Step 3 of said con pounds of general formula (VII) with said compounds of formula (IX) is carried out in the presence of a copper salt and sodium ascorbate in a mixture of protic organic solvent and water.

7. The process according to claim 6, wherein the reaction of Step 2 is carried out in the presence of $Et_3N$ in tetrahydrofuran (THF) and the reaction is carried out at a temperature range of 25-75° C.

8. The process according to claim 6, wherein, in the reaction of Step 3, the copper salt is $CuSO_4.5H_2O$ and the mixture of protic organic solvent and water is a mixture of t-BuOH:$H_2O$ 1:1 and the reaction is carried out at room temperature.

9. A pharmaceutical composition which comprises the compound according to claim 1, or a pharmaceutically acceptable salt thereof, and a pharmaceutically acceptable carrier, adjuvant or vehicle.

\* \* \* \* \*

UNITED STATES PATENT AND TRADEMARK OFFICE
CERTIFICATE OF CORRECTION

PATENT NO. : 9,902,711 B2
APPLICATION NO. : 15/106398
DATED : February 27, 2018
INVENTOR(S) : Félix Cuevas-Cordobés et al.

Page 1 of 1

It is certified that error appears in the above-identified patent and that said Letters Patent is hereby corrected as shown below:

On the Title Page

Foreign Application Priority Data: "13384005" should be -- 13384005.8 --.

In the Claims

Column 86, Line 61: "1,2,3-triazol-yl)" should be -- 1,2,3-triazol-4-yl) --.

Signed and Sealed this
Fourth Day of September, 2018

Andrei Iancu
*Director of the United States Patent and Trademark Office*